United States Patent
Prakash et al.

(10) Patent No.: US 10,660,857 B2
(45) Date of Patent: May 26, 2020

(54) BACTERIAL COMPOSITIONS FOR PROPHYLAXIS AND TREATMENT OF DEGENERATIVE DISEASE

(75) Inventors: Satya Prakash, Brossard (CA); Mitchell Lawrence Jones, Montreal (CA); Christopher Martoni, Montreal (CA)

(73) Assignee: UAS Laboratories LLC, Wausau, WI (US)

( * ) Notice: Subject to any disclaimer, the term of this patent is extended or adjusted under 35 U.S.C. 154(b) by 877 days.

(21) Appl. No.: 13/111,105

(22) Filed: May 19, 2011

(65) Prior Publication Data

US 2011/0217368 A1 Sep. 8, 2011

Related U.S. Application Data

(63) Continuation-in-part of application No. PCT/CA2010/000660, filed on Apr. 30, 2010.

(60) Provisional application No. 61/174,740, filed on May 1, 2009.

(51) Int. Cl.
| | |
|---|---|
| A61K 35/747 | (2015.01) |
| A61K 35/744 | (2015.01) |
| C12N 1/20 | (2006.01) |
| A61K 9/16 | (2006.01) |
| C12R 1/225 | (2006.01) |
| C12N 11/10 | (2006.01) |
| A61K 9/50 | (2006.01) |
| A23C 9/123 | (2006.01) |
| A23L 33/135 | (2016.01) |

(52) U.S. Cl.
CPC .......... *A61K 9/1664* (2013.01); *A23C 9/1234* (2013.01); *A23L 33/135* (2016.08); *A61K 9/5036* (2013.01); *A61K 35/744* (2013.01); *A61K 35/747* (2013.01); *C12N 1/20* (2013.01); *C12N 11/10* (2013.01); *C12R 1/225* (2013.01); *A23C 2220/204* (2013.01); *A23V 2002/00* (2013.01); *A23Y 2220/71* (2013.01)

(58) Field of Classification Search
None
See application file for complete search history.

(56) References Cited

U.S. PATENT DOCUMENTS

| | | | |
|---|---|---|---|
| 4,362,711 A | 12/1982 | Cerami et al. | |
| 5,534,253 A * | 7/1996 | Casas et al. | 424/93.45 |
| 6,217,859 B1 | 4/2001 | Chang et al. | |
| 6,365,148 B1 | 4/2002 | Kim et al. | |
| 6,653,062 B1 | 11/2003 | DePablo et al. | |
| 6,811,786 B1 | 11/2004 | Farmer et al. | |
| 6,919,172 B2 | 7/2005 | DePablo et al. | |
| 7,169,606 B2 | 1/2007 | DePablo et al. | |
| 7,223,543 B2 * | 5/2007 | Stanton et al. | 435/134 |
| RE40,023 E * | 1/2008 | DeSimone | 424/93.4 |
| 7,629,161 B2 * | 12/2009 | Laffend et al. | 435/252.3 |
| 7,939,061 B2 | 5/2011 | Prakash et al. | |
| 8,067,017 B2 * | 11/2011 | Truong-Le | 424/400 |
| 2007/0116671 A1 | 5/2007 | Prakash et al. | |
| 2010/0074933 A1 | 3/2010 | Prakash et al. | |

FOREIGN PATENT DOCUMENTS

| | | |
|---|---|---|
| DE | 19956400 B4 | 9/2005 |
| EP | 2419114 B1 | 4/2016 |
| WO | WO9305161 A1 | 3/1993 |
| WO | WO02/09515 A1 | 2/2002 |
| WO | 2004076657 | 9/2004 |
| WO | 2006042132 A2 | 4/2006 |
| WO | 20070140613 | 12/2007 |
| WO | 2008028300 | 3/2008 |
| WO | WO2008056983 A1 | 5/2008 |
| WO | 2008127180 | 10/2008 |
| WO | WO2010124387 A1 | 11/2010 |

OTHER PUBLICATIONS

Capela et al. "Effect of cryoprotectans, prebiotics and microencapsulation on survival of probiotic organisms in yogurt and freeze-dried yoghurt". Food Research International. 2006, 39: 203-211.*
Irmak et al. Lipids, 2006, vol. 41, No. 8, pp. 771-776.*
Fávaro-Trindade, C.S., et al. " Microencapsulation of L. acidophilus (La-05) and B. lactis (Bb-12) and evaluation of their survival at the pH values of the stomach and in bile", Journal of Microencapsulation, 2002, pp. 485-494, vol. 19, No. 4.
De Boever, P. et al., "Protective effect of the bile salt hydrolase-active Lactobacillus reuteri against bile salt cytotoxicity", Applied Microbiology and Biotechnology, Jun. 2000, pp. 709-714, vol. 53, No. 6.
Martoni, et al., "Microencapsulated bile salt hydrolase producing lactobacillus reuteri for oral targeted delivery in gastrointestinal tract", Appl Mircobiol Biotechnol, 2008, vol. 81, No. 2, pp. 225-233.
Taranto, et al., "Effect of lactobacillus reuteri on the prevention of hypercholesterolemia in mice", J. Dairy Sci., 2000, vol. 83, No. 3, pp. 401-403.

(Continued)

*Primary Examiner* — Vera Afremova
(74) *Attorney, Agent, or Firm* — Kaplan IP Law, P.C.; Jonathan M. Kaplan

(57) ABSTRACT

The disclosure provides an oral composition for reducing serum cholesterol, serum lipids, body fat, or atherogenic index or for prophylaxis or treatment of atherosclerosis, cardiovascular or cerebrovascular diseases, comprising a highly bsh active bacteria, isolate or supernatant thereof; wherein the highly bsh active bacteria degrades >50 μmol glycodeoxycholic acid (GDCA)/gram/hour and >2 μmol taurodeoxycholic acid (TDCA)/gram/hour when measured over 1 hour and 5 hours, respectively, or degrades >65 μmol GDCA/g/hr and >7 μmol TDCA/g/hr when measured over 30 minutes.

22 Claims, 8 Drawing Sheets

(56) References Cited

OTHER PUBLICATIONS

Taranto, et al., "Evidence for hypocholesterolemic effect of lactobacillus reuteri in hypercholesterolemic in mice", J. Dairy Sci., 1998, vol. 81, No. 9, pp. 2336-2340.
Taranto, et al., "Bile salts hydrolase plays a key role on cholesterol removal by lactobacillus reuteri", Biotechnology Letters, 1997, vol. 19, No. 9, pp. 845-847.
De Smet, et al., "Cholesterol lowering in pigs through enhanced bacterial bile salt hydrolase activity", British Journal of Nutrition, 1998, vol. 79, No. 2, pp. 185-194.
Dobrogosz, W., "Enhancement of human health with lactobacillus reuteri: A probiotic, immunobiotic and immunoprobiotic", Nutrafoods, 2005, vol. 4, No. 2/3, pp. 15-28.
Casas and Dobrogosz, "Validation of the probiotic concept: Lactobacillus reuteri confers broad-spectrum protection against disease in humans and animals," Microbial Ecology in Health and Disease, 2000, vol. 12, pp. 247-285.
Angulo, P., "Nonalcoholic fatty liver disease." N. Engl. J. Med., 2002, pp. 1221-1231, vol. 346, No. 16.
Aso, Y. et al.' "Preventive Effect of A Lactobacillus casei Preparation on the Recurrence of Superficial Bladder Cancer in A Double-Blind Trial," European Urology, 1995, vol. 27, No. 2, pp. 104-109.
Chang, T.M.S. "Semipermeable microcapsules", Science, 1964, vol. 146, No. 3643, pp. 524-525.
Chang, T.M. & Prakash, S. Artificial cells for bioencapsulation of cells and genetically engineered *E. coli*. For cell therapy, gene therapy, and removal of urea and ammonia. Methods Mol. Biol. 63, 343-358 (1997).
Chang,T.M. & Prakash,S. Therapeutic uses of microencapsulated genetically engineered cells. Mol. Med. Today 4, 221-227 (1998).
Garrigues, C., et al.,"Characterisation of *Bifidobacteriuim animalis* subsp. *lactis* BB-12 and other probiotic bacteria using genomics, transcriptomics and proteomics", The Australian Journal of Technology, 2005, pp. 84-92, vol. 60, No. 2.
Ford, E.S. et al., "Prevalence of metabolic syndrome among US adults: findings from the third National Health and Nutrition Examination Survey", JAMA, 2002, vol. 287, No. 3, pp. 356-359.
Gaist, D. et al., "Lipid-lowering drugs and risk of myopathy: A population based follow-up study", Epidemiology, 2001, vol. 12, No. 5, pp. 565-569.
Gaist, D. et al., "Statins and risk of polyneuropathy—A case-control study", Neurology, 2002, vol. 58, No. 9, 1333-1337.
Goldenberg, I., et al., "Update on the use of fibrates: focus on bezafibrate", Vascular Health and Risk Management, 2008, vol. 4, No. 1, pp. 131-141.
Hallikainen, M. A. and Uusitupa, M. I. J. , "Effects of 2 low-fat stanol ester-containing margarines on serum cholesterol concentrations as part of a low-fat diet in hypercholesterolemic subjects", Am. J. Clin. Nutr., 1999, vol. 69, No. 3, pp. 403-410.
Huang, J.S. et al., "Efficacy of probiotic use in acute diarrhea in children: a meta-analysis," Digestive Diseases and Sciences, 2002, vol. 47, No. 11, pp. 2625-2634.
Jenkins, D. J. A. et al., "The effect on serum lipids and oxidized low-density lipoprotein of supplementing self-selected low-fat diets with soluble-fiber, soy, and vegetable protein foods", Metabolism, 2000, vol. 49, No. 1, pp. 67-72.
Jones et al. "Method for Bile Acid Determination by High Performance Liquid Chromatography". J Med Sci 2003, vol. 23, No. 5, pp. 277-280.
Lodinova-Zadnikova, R. and Sonnenborn, U., "Effect of preventive administration of a Nonpathogenic *Escherichia coli* strain on the colonization of the Intestine with Microbial Pathogens in Newborn Infants," Biology of the Neonate, 1997, vol. 71, No. 4, pp. 224-232.
Lopez-Garcia, E, et al., "Consumption of Trans Fatty Acids Is Related to Plasma Biomarkers of Inflammation and Endothelial Dysfunction", The Journal of Nutrition, 2005, vol. 135, No. 3, pp. 562-566.
McIntosh, G. H., et al., "A probiotic strain of L. acidophilus reduces DMH-induced large intestinal tumors in male Sprague-Dawley rats," Nutr. Cancer, 1999, vol. 35, No. 2, pp. 153-159.
Omar, M. A. and J. P. Wilson, "FDA adverse event reports on statin-associated rhabdomyolysis", The Annals of Pharmacotherapy, 2002, vol. 36, No. 2, pp. 288-295.
Ornish, D. et al., "Can Life-Style Changes Reverse Coronary Heart-Disease", Lancet, 1990, vol. 336, pp. 129-133.
Pedersen, T. R. et al., "Randomized Trial of Cholesterol-Lowering in 4444 Patients with Coronary-Heart-Disease—the Scandinavian Simvastatin Survival Study (4S)", Lancet, 1994, vol. 344, No. 19, pp. 1383-1389.
Pepys, M.B. et al.,"Targeting C-reactive protein for the treatment of cardiovascular disease", Nature, 2006, vol. 440, pp. 1217-1221.
Prakash, S. and Jones, M.L., "Engineering Artificial Cells for Therapy", 2nd World Engineering Congress, Sarawak, Malaysia, Jul. 22-25, 2002, pp. 1-6, Ref Type: Conference Proceeding.
Urbanska A.M., et al., "Estimation of the Potential Antitumor Activity of Microencapsulated Lactobacillus acidophilus Yogurt Formulation in the Attenuation of Tumorigenesis in Apc(Min/+) Mice", Dig. Dis. Sci., 2009, vol. 54, pp. 264-273.
Probstfield, J. L. and B. M. Rifkind, "The Lipid Research Clinics Coronary Primary Prevention Trial: design, results, and implications," Eur. J. Clin. Pharmacol, 1991, 40 Suppl 1, S69-S75.
Rayes, N. et al., "Early enteral supply of lactobacillus and fiber versus selective bowel decontamination: a controlled trial in liver transplant recipients," Transplantation, 2002, vol. 74, No. 1, pp. 123-128.
Scalia S.' "Simultaneous determination of free and conjugated bile acids in human gastric juice by high-performance liquid chromatography". J of Chrom, 1988, vol. 431, pp. 259-269.
Sgro, C. and Escousse, A., "Side-Effects of fibrates (except liver and muscle)", Therapie, 1991, vol. 46, No. 5, 351-354 (abstract in English).
Staffa, J. A., et al., "Cerivastatin and reports of fatal rhabdomyolysis," N. Engl. J. Med., 2002, vol. 346, No. 7, 533-540.
Szajewska, H. et al., "Efficacy of Lactobacillus GG in prevention of nosocomial diarrhea in infants," J. Pediatr., 2001, vol. 138, No. 3, pp. 361-365.
Tabas, K. J., et al., "Subendothelial lipoprotein retention as the initiating process in atherosclerosis—Update and therapeutic implications", Circulation, 2007, vol. 116, No. 16, pp. 1832-1844.
Tall, A. R. "An overview of reverse cholesterol transport", European Heart Journal, 1998, 19 Supplement A, A31-A35.
"Third Report of the National Cholesterol Education Program (NCEP) Expert Panel on Detection, Evaluation, and Treatment of High Blood Cholesterol in Adults (Adult Treatment Panel III) final report", National Institutes of Health, 2002.
Tobias, P.S. and Curtiss, L.K., "Toll-like receptors in atherosclerosis," Biochem Soc Trans., 2007, vol. 35, No. 6, pp. 1453-1455.
Uludag, H., et al.. Technology of mammalian cell encapsulation. Adv. Drug Deliv. Rev., 2000, vol. 42, pp. 29-64.
Shah, N.P. and Ravula, R.R., "Microencapsulation of probiotic bacteria and their survival in frozen fermented dairy desserts", Australian Journal of Dairy Technology, 2000, pp. 139-144, vol. 55, No. 3.
Thornton, G., et al., Bile tolerance and bile salt hydrolase activity of lactobacilli and bifidobacteria isolated from the human intestine, Gastroenterology, 1995, vol. 108, No. 4, AGA Abstracts, A928.
Corzo, G., et al., "Measurement of bile salt hydrolase activity from Lactobacillus acidophilus based on disappearance of conjugated bile salts", Journal of Dairy Science, 1999, pgs. 466-471, vol. 82, No. 3.
Christiaens, H., et al., "Cloning and Expression of a Conjugated Bile Acid Hydrolase Gene from Lactobacillus plantarum by Using a Direct Plate Assay", Applied and Environmental Microbiology, 1992, pp. 3792-3798, vol. 58, No. 12.
Liu, P. and Krishnan, T.R., "Alginate-Pectin-Poly-L-lysine Particulate as a Potential Controlled Release Formulation", Journal of Pharm. Pharmacology, 1999, pp. 141-149, vol. 51.
De Smet, I. et al., "In vitro study of bile salt hydrolase (BSH) activity of BSH isogenic Lactobacillus plantrarum 80 strains and estimation of cholesterol lowering through enhanced BSH activity", Microbial Ecology in Health and Disease, 1994, pp. 315-329, vol. 7, No. 6.

(56) References Cited

OTHER PUBLICATIONS

Ahn Y.T., et al., "Bile Salts Deconjugation of Lactic Acid Bacteria Found in the Feces of Normal Korean Adults and in Fermented Milk Products", Kor. J. Anim. Sci., 1999, pp. 183-192, vol. 41, No. 2.

Ahn, Y.T., et al., "Study on Bile Salts Deconjugation of Lactic Acid Bacteria Found in the Feces of Normal Korean Adults in Fermented Milk Products", Journal of Korean Livestock, 1999, pp. 183-192, vol. 41, No. 2 (translation).

De Smet et al. 1995 (Journal of Applied Bacteriology; 79; 292-301; 1995).

Grillet al. (Canadian Journal of Microbiology; 46; 10; 878-884; 2000).

Jiang et al. (Ann Microbiol (2010) 60:81-88).

Lye et al. (Intl. Dairy Journal 20 (2010) 169-175).

Sridevi et al. Hypocholesteremic Effect of Bile Salt Hydrolase from Lactobacillus buchneri ATCC 4005, Food Res. Int'l 42:516-520 (2009).

Prakash, Satya et al. U.S. Appl. No. 61/174,740, filed May 1, 2009.

Du Toit et al., "Characterisation and selection of probiotic lactobacilli for a preliminary minipig feeding trial and their affect on serum cholesterol levels, faeces pH and faeces moisture content," International Journal of Food Microbiology, 1998, vol. 40, pp. 93-104.

Tanaka et al., "Bile Salt Hydrolase of Bifidobacterium longum-Biochemical and Genetic Characterization," Applied and Environmental Microbiology, 2000, vol. 66, No. 6, pp. 2502-2512.

Vera et al., "Comparative study of culture media used for sourdough lactobacilli," Food Microbiology, 2009, 26(7), pp. 728-733.

Meroth et al., "Monitoring the Bacterial Population Dynamics in Sourdough Fermentation Processes by Using PCR-Denaturing Gradient Gel Electrophoresis," Applied and Environmental Microbiology, 2003, vol. 69, No. 1, pp. 175-482.

Savini et al., "Pilot-scale Production and Viability Analysis of Freeze-Dried Probiotic Bacteria Using Different Protective Agents," Nutrients, 2010, vol. 2, pp. 330-339.

Hubalek et al., "Protectants used in the cryopreservation of microorganisms," Cryobiology, 2003, vol. 46, pp. 205-229.

Coakley et al., "Conjugated linoleic acid biosynthesis by human-derived *Bifidobacterium* species," Journal of Applied Microbiology, 2003, vol. 94, pp. 138-145.

Naser et al., "Identification of lactobacilli by pheS and rpoA gene sequence analyses," International Journal of Systematic and Evolutionary Microbiology, 2007, vol. 57, pp. 2777-2789.

Begley et al., "Bile Salt Hydrolase Activity in Probiotics," Applied and Environmental Biology, 2006, vol. 72, No. 3, pp. 1729-1738.

Gleiss & Grobe, Notice of Opposition filed on behalf of N.V. Nutricia against UAS Laboratories LLC for EP patent No. 2419114B1 dated Apr. 20, 2016.

\* cited by examiner

BACTERIAL COMPOSITIONS FOR PROPHYLAXIS AND TREATMENT OF DEGENERATIVE DISEASE

RELATED APPLICATIONS

This application is a continuation-in-part of PCT/CA2010/000660 filed on Apr. 30, 2010, which claims the benefit of priority from U.S. provisional application No. 61/174,740 filed May 1, 2009, the contents of both of which are incorporated herein by reference in their entirety.

FIELD

The present disclosure relates to an improved oral composition of a highly bsh active bacteria, isolate or supernatant thereof and processes for preparing the improved composition. The present disclosure also relates to methods and uses of the improved oral composition for reducing serum cholesterol, serum lipids, body fat, or atherogenic index and for prophylaxis and treatment of atherosclerosis, cardiovascular or cerebrovascular diseases.

BACKGROUND

Hypercholesterolemia and Coronary Artery Disease

Coronary artery disease (CAD) is the leading cause of death, the most common form of heart disease and the most common cause of sudden death in the western world. Clinical and epidemiological evidence have established a clear link between elevated serum cholesterol and CAD. Within apparently healthy populations, there is an exponential relation between serum cholesterol and coronary risk. In middle age, the risk of CAD increases by 2 to 3% for each 1% increase in cholesterol levels.

An estimated 107 million American adults have total serum cholesterol levels of 5.18 mmol/l (200 mg/dL) and higher. Of these, approximately 37 million have levels of 6.22 mmol/l (240 mg/dL) or above. In adults, total cholesterol levels of 6.22 mmol/l or higher are considered high risk for cardiovascular related events while levels between 5.18 and 6.22 mmol/l are considered borderline high risk. According to the recommendations of the National Cholesterol Education Program's (NCEP) the primary objective of any therapy is the lowering of LDL Cholesterol levels (Third Report of the NCEP Expert Panel 2002). New guidelines now consider other risk factors such as age, family history, smoking, hypertension, low HDL, and diabetes mellitus, in estimating cut-off levels of cholesterol requiring intervention. LDL goals in primary prevention therefore depend on a patient's absolute risk for CAD related events in the short term or long term. Currently, according to the recently revamped recommendations of the NCEP, an additional 36 million US citizens should be treated for high cholesterol. Currently, less than half of patients who qualify for lipid modifying treatment are receiving it and only a third of treated patients are achieving their LDL cholesterol goal.

Pathogenesis of Atherosclerosis

The involvement of elevated LDL cholesterol in atherosclerosis and CAD is well documented. Atherosclerosis is initiated by the retention of apolipoprotein B-containing lipoproteins (e.g. LDL cholesterol) in the arterial wall. Over time, lipoproteins retained in the arterial wall become modified (i.e. aggregated and oxidized) and elicit a cascade of biological responses that develop into a maladaptive inflammatory response (Tabas et al. 2007). In particular, monocytes enter the subendothelium, differentiate into macrophages and ingest the retained modified lipoproteins to become cholesterol-laden foam cells. Eventually, inflammatory cells enter the lesions and help contribute to the aforementioned maladaptive inflammatory response, a process accelerated by amplified retention of lipoproteins in established lesions. A process mediated by cytokines and growth factors causes smooth muscle cells to migrate and form a collagenous fibrous cap (mature atherosclerotic plaque), most likely as a scar-like response to wall off the lesion (Tabas et al. 2007). However, as the lesion progresses, macrophages die, resulting in areas of necrosis containing extracellular debris, cholesterol crystals, proteases and thrombotic material. At this point, fibrous cap thinning, plaque eruption or erosion may occur, potentially leading to acute thrombotic vascular events such as myocardial infarction and stroke.

High-density lipoproteins play a key role in "reverse cholesterol transport", a pathway by which excess cholesterol is removed from extrahepatic cells and returned to the liver for excretion from the body. In the peripheral tissues, HDL is believed to remove cellular cholesterol through a variety of mechanisms including interaction of HDL apolipoproteins with cell-surface binding sites or receptors (Tall, 1998). The action of lecithin-cholesterol acyltransferase (LCAT) converts the absorbed cholesterol into cholesterol esters and in turn can increase the absorption capacity of HDL. Upon return to the liver, cholesterol may be metabolized into bile salts and excreted from the body. LDL and HDL cholesterol are the major factors in maintaining the cholesterol balance of the body and a high ratio of HDL to LDL correlate well with a lower incidence of CAD in humans.

High serum triglyceride levels are similarly a risk factor for atherosclerosis and CAD. Specific reasons for this include the increased production of atherogenic chylomicron and VLDL remnants, the inverse relationship present between serum triglyceride and HDL, the possible resultant increase in LDL attributable to remnant-reduced hepatic LDL-receptors as well as the formation of more dense and, therefore, more atherogenic LDL, and to the interaction between serum triglyceride and the fibrinolytic/coagulation system. Because of the multiple links between elevated triglyceride levels and risk for atherosclerotic cardiovascular disease, screening for hypertriglyceridemia is important when determining a patient's risk for atherosclerotic cardiovascular disease.

Immune Responses in Atherosclerosis

The pathogenesis of atherosclerosis is believed to include dyslipidemia, vascular endothelium dysfunction, and a chronic inflammatory process. Several mediators have been shown to be involved in intercellular signaling in atherosclerosis, including small molecules such as nitric oxide, lipid mediators such as eicosanoids and sterols and cytokines. Inflammation is mediated by cytokines, glyco-proteins involved in cell to cell signaling, which are produced by macrophages and dendritic cells in the epithelium in response to an antigenic or foreign body stimulus. The immune response is implicated in the formation of early fatty streaks, when the endothelium is activated and expresses chemokines and adhesion molecules leading to monocyte/lymphocyte recruitment and infiltration into the subendothelium. It also acts at the onset of adverse clinical vascular events, when activated cells within the plaque secrete matrix proteases that degrade extracellular matrix proteins and weaken the fibrous cap, leading to rupture and thrombus formation. Recently, toll-like receptors (TLR) on the surface of the gastrointestinal epithelium have been linked to the induction of an inflammatory response, helping to initiate the start signal for the production of pro-inflammatory cytokines (Tobias and Curtiss, 2007).

Specific emphasis is placed on the contribution of pro- and anti-inflammatory cytokines to pathogenic (innate and adaptive) and regulatory immunity in the context of atherosclerosis. Cytokines can be differentiated by those with an essentially pro-inflammatory mode of action, including tumor necrosis factor (TNF-alpha), interleukin-12, IL-18 and interferon gamma from those with anti-inflammatory mode of action, including IL-4, IL-10, IL-13 and the endogenous IL-1 receptor antagonist IL-1ra. In response to the local milieu of cytokines, $CD4^+$ cells differentiate into the Th1 (pro-inflammatory) or Th2 (anti-inflammatory) lineage. Among the principal inducers of the Th1 and Th2 cells are IL-12 and IL-10, respectively. Cytokines involved in the Th1 process include IL-2, IFN-gamma and TNF, while those involved in the Th2 process include IL-3, IL-4, IL-5, IL-6, IL-10 and IL-13. Over 30 major members of the interleukin family have been identified, the majority of which play a role in atherogenesis. Specifically, they have been attributed to primarily anti-atherogenic (IL-1ra, IL-9, IL-10, IL-11) and pro-atherogenic (IL-1, IL-2, IL-6, IL-18) properties. Modulating these interleukins represent the most readily applicable approach to immunotherapy in atherosclerosis. It is believed that gut bacteria initiate an inflammatory response when epithelium TLRs recognize non-commensal microbial motifs and this cytokine signal may translate to increased risk of atherosclerosis. The corollary of this response is that commensal microflora are required to maintain gut homeostasis through the recognition of their non-inflammatory motifs by TLRs. Recent research has shown that pro-inflammatory cytokines produced in the gut can be greatly decreased by delivering commensal bacteria (*Lactobacillus acidophilus*) delivered free in saline or in fermented milk (Urbanska et al. 2009). This research showed that *L. acidophilus* decreased IL-6, IL-12, TNF-alpha, and IFN-gamma levels when administered orally in saline and in fermented milk (only IL-6 data was published) (Prakash and Urbanska 2007).

In addition to pro- and anti-inflammatory cytokines, high sensitivity C-reactive protein is arguably the most important serum inflammatory marker of coronary risk. Recent research suggests that patients with elevated basal levels of CRP are at an increased risk of cardiovascular disease as well as diabetes, and hypertension. A clinical study of 700 nurses showed that those in the highest quartile of trans fat consumption had blood levels of C-reactive protein that were 73% higher than those in the lowest quartile (Lopez-Garcia, 2005). Others have shown that CRP can exacerbate ischemic necrosis in a complement-dependent fashion and that CRP inhibition can be a safe and effective therapy for myocardial and cerebral infarcts (Pepys et al. 2006).

Metabolic Syndrome

Dyslipidemia, atherosclerosis, and chronic inflammation are connected to other degenerative diseases through the metabolic syndrome. Metabolic syndrome is characterized by a group of metabolic risk factors in one individual and increases the individual's risk of developing atherosclerosis, cardiovascular disease, cerebrovascular disease and diabetes. This constellation of signs and symptoms affects one in five people, and prevalence increases with increasing age. Some studies estimate the prevalence in the USA to be up to 25% of the population (Ford et al., 2002). Symptoms and features include: Fasting hyperglycemia—diabetes mellitus type 2 or impaired fasting glucose, impaired glucose tolerance, or insulin resistance; High blood pressure; Central obesity (also known as visceral, male-pattern or apple-shaped adiposity), overweight with fat deposits mainly around the waist.

Non-Alcoholic Fatty Liver Disease (NAFLD)

Non-alcoholic fatty liver disease (NAFLD) is considered to be a hepatic manifestation of the metabolic syndrome. NAFLD is defined as fatty inflammation of the liver when this is not due to excessive alcohol use. NAFLD is strongly associated with obesity, dyslipidaemia, insulin resistance (IR) and type II (non-insulin dependent) diabetes mellitus. NAFLD covers the full spectrum of metabolic fatty liver disorders, particularly when histology is undefined. NAFLD can manifest as simple steatosis (fatty liver), at the most clinically indolent extreme, or can progress to steatosis with inflammation or fibrosis, in which case it is termed NASH. However, even stable forms of NAFLD may carry as yet unidentified morbidity since fatty liver typically functions less efficiently than non-fatty liver. NASH likely represents an intermediate stage characterized by steatosis with lobular inflammation. NAFLD is known to affect 10-39% of the general global population with an average incidence of 20% (Angulo 2002).

There are several risk factors associated with NAFLD. These factors include common life conditions and diseases such as obesity, hyperglycemia, type 2 diabetes mellitus, and hypertriglyceridemia. In addition, NAFLD is strongly associated with central obesity and visceral adiposity. Genetic and racial factors are also associated with NAFLD/NASH. This disorder will therefore contribute substantially to the burden of chronic liver disease in coming decades.

Treatment and Prevention of Hypercholesterolemia and Dyslipidemia

Methods for lowering cholesterol levels in humans involve dietary management, behaviour modification, and exercise and drug therapy. Dietary intervention alone is insufficient for most individuals. Studies show that complete elimination of dietary cholesterol and limiting fat content to less than ten percent of the daily caloric intake results in only a four percent regression of atherosclerotic plaques after five years when combined with stress management and aerobic exercise (Ornish et al. 1990).

Additional dietary options for LDL cholesterol lowering have been proposed, including soluble fibres, plant sterols and stanols and soy protein. Recent reports indicate that soluble forms of dietary fibre at 5-10 g per day can reduce LDL cholesterol by approximately 5% (Third Report of the NCEP Expert Panel 2002). Little, no, or inconsistent effects have been reported in regards to HDL cholesterol; however, it appears that modulation of cholesterol and bile metabolic pathways may be required as much evidence from studies that attempt to lower dietary intake or increase cholesterol catabolism result in decreases in HDL unless used in combination with cholesterol lowering medication that affects liver enzymes. Furthermore, insoluble fibre has not been shown to significantly affect circulating cholesterol levels. Animal and human studies show that plant stanols and sterols reduce plasma total cholesterol and low density lipoprotein (LDL) cholesterol levels. Data has shown that plant-derived sterol and stanol esters at dosages of 2-3 g/day decrease LDL cholesterol levels by 6-15% with no significant change in triglyceride or HDL cholesterol levels (Hallikainen and Uusitupa, 1999). Again, often studies that show no decrease in HDL or an non-statistically significant decrease in HDL have included patients on cholesterol lowering medication that alters liver enzymatic pathways such as Statins. Soy protein included in a diet low in saturated fatty acids and cholesterol has been shown to lower LDL cholesterol by about 5%, however, dosage requirements are not well known (Jenkins et al. 2000).

Statins can significantly reduce endogenous cholesterol synthesis, through inhibition of HMG-CoA reductase, and upregulate low-density lipoprotein receptors in the liver, leading to reductions in LDL-C of 20-30%. The efficacy of statins has been thoroughly evaluated in a multitude of clinical trials (Pedersen et al. 1994). Statins, however, have been shown to exhibit rare, but potentially severe, side-effects. The most predominant of these are myopathy, which may evolve into life-threatening rhabdomyolysis, and polyneuropathy (Gaist et al. 2001; Gaist et al. 2002; Omar and Wilson 2002; Staffa et al. 2002).

Fibrate therapy has also been shown to offer long-term benefits in high-risk patients with low HDL cholesterol-high triglyceride dyslipidemia (Goldenberg et al. 2008). Fibrates, however, are also associated with a variety of adverse effects including increased risk of gall stones, myopathy and stomach upset (Sgro and Escousse, 1991).

Niacin has been used for quite some time now, at doses of 1-2 grams per day, to reduce triglycerides and lower LDL-C. Interestingly, vitamin B3 has been shown to increase HDL-C at these levels as well and has been prescribed to patients with low HDL-C who are at risk of suffering a cardiac event. Unfortunately, uncomfortable and severe side effects including facial and full body flushing are exhibited with regular use.

Bile acid sequestrants (BAS) have been used clinically since the 1960s for lowering of LDL cholesterol. Bile acid sequestrants have a low rate of compliance caused, in part, by gastrointestinal side effects (Probstfiled and Rifkind, 1991).

Probiotics

Probiotics have been reported to be associated with a range of clinically relevant health benefits. Various strains of lactic acid bacteria have been particularly well studied in humans and animals. Placebo controlled clinical trials have shown *L. reuteri, L. rhamnosus* GG, *L. casei* and *S. boulardii* to be effective in reducing the duration of acute diarrhea (Huang et al. 2002). *L. rhamnosus GG* administered to infants reduced the risk of nosocomial diarrhea and rotavirus gastroenteritis (Szajewska et al. 2001). Studies by Aso et al. revealed that *L. casei* Shirota increases the percentage of T-helper cells and NK cells in adult colorectal cancer patients and has a protective effect on the recurrence of superficial bladder cancer (Aso et al., 1995). In addition, select strains of lactobacilli have been shown to significantly suppress intestinal tumors by chemical mutagens (McIntosh et al. 1999). Lactic acid bacteria have been administered to prevent sepsis in patients with severe acute pancreatitis. A randomized study by Rayes et al. involving liver transplant patients revealed postoperative infections were significantly reduced by feeding live *L. plantarum* cells in comparison to standard antibiotic treatment (Rayes et al. 2002). As a means of preventing allergy, a randomized controlled study by Lodinova-Zadnikova et al. investigated the effect of at birth colonization with nonpathogenic *Escherichia coli* Nissle 1917 (Lodinova-Zadnikova and Sonnenborn 1997). Subjects inoculated with the *E. coli* strain showed significantly reduced colonization of bacterial pathogens as well as significantly lower incidence of allergies after 10 and 20 years in comparison with control subjects. Probiotics have also been used as treatment options for managing Inflammatory Bowel Diseases (IBD) such as Crohn's disease, ulcerative colitis and pouchitis.

*L. reuteri* is well-established as one of the most ubiquitous members of the naturally-occurring gut bacteria. Host-specific strains of *L. reuteri* have been documented to confer broad-spectrum protection from an assortment of microbial and chemical associated disease in humans and animals (Dobrogosz, 2005). However, traditional probiotic therapy involves administration of bacteria with the hope that some bacteria will survive the harsh gastric conditions and colonize the colon where the bacteria will reproduce and live indefinitely. Far fewer bacteria survive in the duodenum, jejunum or ileum because of factors such as acidity, immune response and bile concentration. Bacteria must be present in the duodenum or jejunum of the small intestine for lowering cholesterol and in particular bile acid.

SUMMARY

The present inventors have determined that highly bile salt hydrolase (bsh) active bacteria provide an improved agent for reducing serum cholesterol, serum lipids, body fat, and atherogenic index and for prophylaxis and treatment of atherosclerosis, cardiovascular and cerebrovascular diseases.

Accordingly, in one aspect, the present disclosure provides an oral composition comprising a highly bsh active bacteria, isolate or supernatant thereof; wherein the highly bsh active bacteria degrades >50 μmol glycodeoxycholic acid (GDCA)/gram/hour and >2 μmol taurodeoxycholic acid (TDCA)/gram/hour when measured over 1 hour and 5 hours, respectively; or degrades >65 μmol GDCA/g/hr and >7 μmol TDCA/g/hr when measured over 30 minutes. In one embodiment, the highly bsh active bacteria degrades >300 μmol GDCA/g/hr and >40 μmol TDCA/g/hr when measured over 30 minutes. In another embodiment, the highly bsh active bacteria degrades >2000 μmol GDCA/g/hr and >500 μmol TDCA/g/hr when measured over 30 minutes. In yet another embodiment, the highly bsh active bacteria degrades >15000 μmol GDCA/g/hr and >2000 μmol TDCA/g/hr when measured over 30 minutes.

In one embodiment, the bacteria is *Lactobacillus, Bifidobacteria, Pediococcus, Streptococcus, Enterococcus*, or *Leuconostoc*. In another embodiment, the *Lactobacillus* is *Lactobacillus reuteri*, optionally, *Lactobacillus reuteri* (NCIMB 701359), *Lactobacillus reuteri* (NCIMB 701089), *Lactobacillus reuteri* (ATCC 55148), *Lactobacillus reuteri* (ATCC 23272), *Lactobacillus reuteri* (NCIMB 702655), *Lactobacillus reuteri* (LMG 18238), *Lactobacillus reuteri* (CCUG 32271), *Lactobacillus reuteri* (CCUG 32305), *Lactobacillus reuteri* (CCUG 37470), *Lactobacillus reuteri* (CCUG 44001) or *Lactobacillus reuteri* (CCUG 44144). In another embodiment, the composition further comprises a carrier.

In yet another embodiment, the concentration of bacteria is $10^6$-$10^{12}$ colony forming units (CFU)/gram.

The bacteria of the present disclosure is optionally contained in a polymer or in a microcapsule or nanocapsule.

In another embodiment, the oral composition described herein is grown under fermentation conditions comprising a carbon source, a nitrogen source, a pH of 4-7, optionally 5, and a harvest time of 6-24 hours, optionally 8-16 hours. In one embodiment, the carbon source comprises maltose, sucrose, dextrin, a combination of sorbitol and glucose or a combination of inulin and glucose. In another embodiment, the nitrogen source comprises (i) yeast extract and malt extract, yeast extract and beef extract, or casein hydrolysate and malt extract; and (ii) peptone or tryptone. In yet another embodiment, the nitrogen source comprises cysteine. In an embodiment, the fermentation conditions further comprise a reducing agent. In one embodiment, the fermentation conditions further comprise cysteine which is both a reducing agent and an additional nitrogen source.

In yet another embodiment, the oral composition described herein is lyophilized with lyoprotectants. In one embodiment, the lyoprotectants comprise a final concentration of 0.2% to 10% maltodextrin and 0.05% to 0.33% yeast extract or 0.05-10%, optionally 0.05-2.5%, inulin and 0.05 to 0.33% yeast extract. In one embodiment, the lyoprotectants comprise a final concentration of 2-4% maltodextrin and 0.1% yeast extract, 0.3% inulin and 0.1% yeast extract, or 0.05-10%, optionally 0.3%, inulin. In another embodiment, the lyoprotectants comprise 0.2% to 10%, optionally 1-3%, maltodextrin and 0.01% to 0.1%, optionally 0.025% to 0.05%, cysteine. In yet another embodiment, the lyoprotectants comprise 0.2% to 10% maltodextrin, 0.01% to 0.1% cysteine and 0.05% to 0.33% yeast extract. In yet another embodiment, the lyoprotectants comprise 0.05 to 10% inulin and 0.01-0.1% cysteine.

In a further embodiment, the oral composition described herein is stored in liquid, wherein the liquid storage conditions comprise a final preservative solution comprising 2.5-10% growth media, 50-99.99% yogurt or other fermented milk, 50-99.99% culture supernatant or 5% MRS solution.

In yet a further embodiment, the oral composition described herein is flash frozen in a final cryoprotectant solution, such as 0.2-10% maltodextrin, optionally 1-3%, maltodextrin and 0.05 to 0.33% yeast extract, optionally 0.1-0.2% yeast extract, 0.05 to 10% inulin, optionally at least 0.2% inulin, 0.5M Trehalose, 0.5M sucrose or fructose, 0.5M lactose, 0.5M maltose or 50-99.99%, optionally 50% spent media. In another embodiment, the oral composition is flash frozen in a final cryoprotectant solution comprising 0.2 to 10%, optionally 1-3%, maltodextrin, 0.01 to 0.1%, optionally 0.025 to 0.05%, cysteine and optionally, 0.05 to 0.33% yeast extract. In yet a further embodiment, the oral composition is flash frozen in a final cryoprotectant solution comprising 0.05% to 10% inulin and 0.01% to 0.1% cysteine.

In another aspect, the oral composition of the present disclosure further comprises a triglyceride lowering agent, an agent for increasing HDL or limiting HDL decrease, a cholesterol lowering agent, an agent for preserving bsh activity, an agent for modulating adipokines or hormones of obesity, a hypoglycemic agent, or a therapeutic for reducing the pro-inflammatory cytokines IL-1α/β, IL-2, IL-15, IL-3, IL-6, IL-8, IL-12, IL-17, IFN-gamma, TNF-alpha, or for increasing the level of the anti-inflammatory cytokines IL-1ra, IL-9, IL-10, IL-11.

In another aspect of the present disclosure, the present inventors provide methods and uses of the oral compositions for reducing serum cholesterol, serum lipids, body fat, or atherogenic index and for prophylaxis and treatment of atherosclerosis, cardiovascular or cerebrovascular diseases in an animal, optionally a mammal, such as a human.

Also provided herein are processes for producing highly bsh active bacteria comprising growing the bacteria under fermentation conditions; lyophilizing the bacteria with lyoprotectant, storing the bacteria under liquid storage conditions and flash freezing the bacteria with cryoprotectants.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

Embodiments of the disclosure will now be described in relation to the drawings in which.

DETAILED DESCRIPTION

Figure 1:
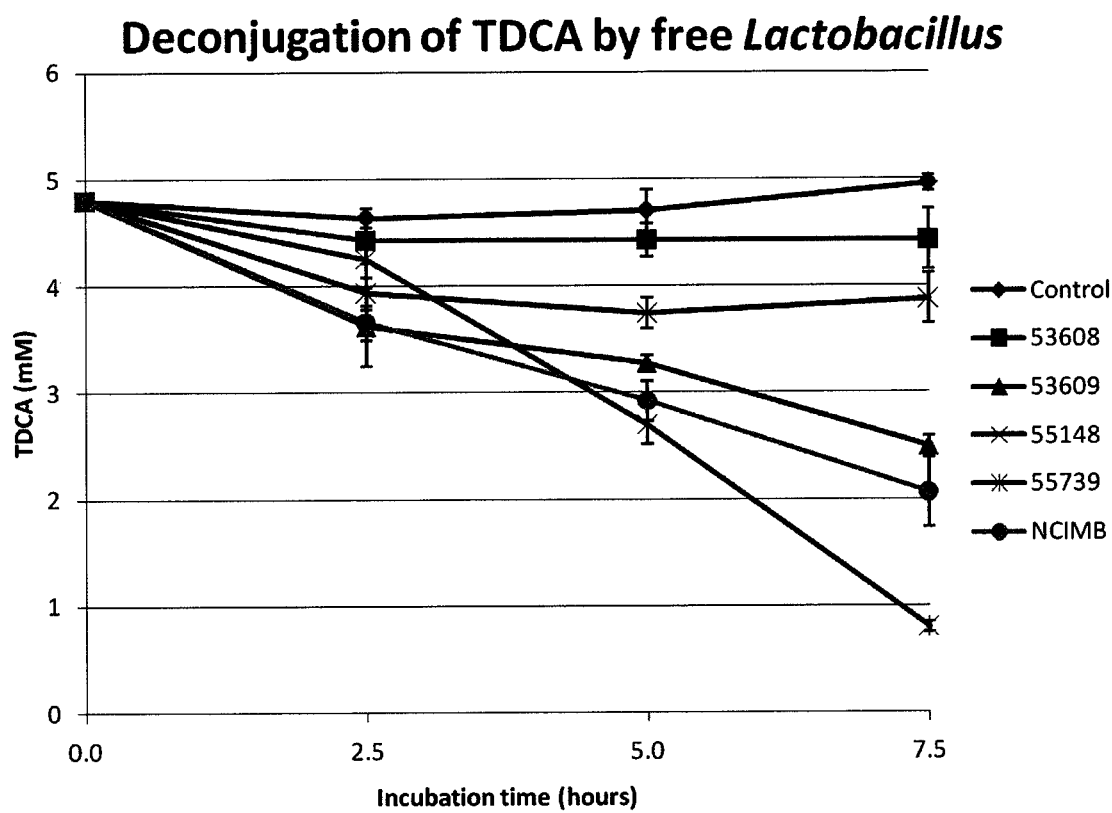
FIG. 1 shows deconjugation of TDCA by free *Lactobacillus reuteri* strains (ATCC 53608, ATCC 53609, ATCC 55148, ATCC 55739, and NCIMB 701359) over time. The experiment was performed in triplicate and error bars represent one standard deviation from the mean.

The present inventors have shown that highly bsh active bacteria provide an improved oral composition for reducing serum cholesterol, serum lipids, body fat, and atherogenic index and for prophylaxis and treatment of atherosclerosis, cardiovascular and cerebrovascular diseases.

Compositions

Accordingly, there is provided an oral composition for reducing serum cholesterol, serum lipids, body fat, or atherogenic index or for prophylaxis or treatment of atherosclerosis, cardiovascular or cerebrovascular diseases, the composition comprising a highly bsh active bacteria, isolate or supernatant thereof; wherein the highly bsh active bacteria degrades >50 µmol glycodeoxycholic acid (GDCA)/gram/hour and >2 µmol taurodeoxycholic acid (TDCA)/gram/hour when measured over 1 hour and 5 hours, respectively; or degrades >65 µmol GDCA/g/hr and >7 µmol TDCA/g/hr when measured over 30 minutes. In one embodiment, the highly bsh active bacteria degrades >300 µmol GDCA/g/hr and >40 µmol TDCA/g/hr when measured over 30 minutes. In another embodiment, the highly bsh active bacteria degrades >2000 µmol GDCA/g/hr and >500 µmol TDCA/g/hr when measured over 30 minutes. In yet another embodiment, the highly bsh active bacteria degrades >15000 µmol GDCA/g/hr and >2000 µmol TDCA/g/hr when measured over 30 minutes.

In one embodiment, the composition further comprises a carrier.

Highly bsh active bacteria as used herein refers to bacteria that degrade >50 µmol GDCA/gram/hour and >2 µmol TDCA/gram/hour when measured over 1 hour and 5 hours, respectively; or degrade >65 µmol GDCA/g/hr and >7 µmol TDCA/g/hr when measured over 30 minutes, optionally >300 µmol GDCA/g/hr and >40 µmol TDCA/g/hr when measured over 30 minutes, or >2000 µmol GDCA/g/hr and >500 µmol TDCA/g/hr when measured over 30 minutes or >15000 µmol GDCA/g/hr and >2000 µmol TDCA/g/hr when measured over 30 minutes and are readily identified by a person skilled in the art based on the methods described in the Examples. In one embodiment, the GDCA and TDCA degradation is measured by HPLC. Determination of bile salts by HPLC is described in Scalia 1988 and Jones et al. 2003.

The term "isolate" as used herein refers to a separated, isolated, or fractionated portion of the cell culture or fermentation product which may be more pure or more active than the crude sample. The term "supernatant" as used herein refers to the liquid overlying the material deposited by settling, precipitating or centrifuging.

In an embodiment, the highly bsh active bacteria are live bacteria. The term "live bacteria" as used herein refers to a biomass of nutrient metabolizing and waste excreting bacteria. In one embodiment, the live bacteria are probiotic bacteria. The term "probiotic bacteria" as used herein refers to live microorganisms which when delivered in adequate amounts confer a health benefit to the host.

The highly bsh active bacteria is optionally *Lactobacillus, Bifidobacteria, Pediococcus, Streptococcus, Enterococcus,* or *Leuconostoc*.

In one embodiment, the *Lactobacillus* is *Lactobacillus reuteri*, optionally, *Lactobacillus reuteri* (NCIMB 701359), *Lactobacillus reuteri* (NCIMB 701089), *Lactobacillus reuteri* (ATCC 55148), *Lactobacillus reuteri* (ATCC 23272), *Lactobacillus reuteri* (NCIMB 702655), *Lactobacillus reuteri* (LMG 18238), *Lactobacillus reuteri* (CCUG 32271), *Lactobacillus reuteri* (CCUG 32305), *Lactobacillus reuteri* (CCUG 37470), *Lactobacillus reuteri* (CCUG 44001) or *Lactobacillus reuteri* (CCUG 44144).

In another embodiment, the *Lactobacillus reuteri* adheres to the gastrointestinal epithelial cells, competes for adhesion, or inhibits the binding of other bacteria due to cell surface proteins.

In an embodiment, the concentration of bacteria in the oral compositions described herein is $10^6$-$10^{12}$ colony forming units (CFU)/gram, optionally $10^8$-$10^{12}$ CFU/gram. In another embodiment, the composition provided herein comprises $10^6$-$10^{14}$ CFU, optionally $10^8$-$10^{13}$ CFU.

The term "bsh" or "bile salt hydrolase" as used herein refers to an enzyme capable of hydrolyzing bile salts produced by the bacteria.

The highly bsh active bacteria can be grown under fermentation conditions that improve biomass production and bsh activity. In one embodiment, the fermentation conditions comprise inoculation in medium comprising a carbon source, and a nitrogen source and having a pH of 4 to 7 and a harvest time of 6 to 24 hours. In a particular embodiment, the pH of the fermentation conditions is 5. In yet another embodiment, the harvest time is 8 to 16 hours.

In one embodiment, the carbon source comprises maltose, sucrose, dextrin, a combination of sorbitol and glucose or a combination of inulin and glucose. In a particular embodiment, the carbon source is maltose. In one embodiment, the carbon sources are added to a final concentration of 2%, for example, if inulin and glucose are used, 1% of each are added to a final concentration of 2%.

In another embodiment, the nitrogen source comprises (i) yeast extract and malt extract, yeast extract and beef extract, or casein hydrolysate and malt extract; and (ii) peptone or tryptone. In yet another embodiment, the nitrogen source comprises cysteine. The peptone may be any peptone, including without limitation, peptone no. 3, fish peptone, soy peptone, proteose peptone and casein peptone. In a particular embodiment, the peptone is peptone no. 3. In one embodiment, the nitrogen source is added to a total of 2.5%, for example, if a peptone, yeast and malt extract source is used, 1% peptone, 0.5% yeast extract and 1% malt extract are added to a final concentration of 2.5%. In another embodiment, beef extract substitutes for malt extract and casein substitutes for either the peptone or yeast extract. In an embodiment, the fermentation conditions further comprise a reducing agent, such as cysteine. In one embodiment 0.01 to 0.1% cysteine is added, optionally 0.01% or 0.025% or 0.05%. Cysteine acts as both a nitrogen source and a reducing agent. As a reducing agent, cysteine helps lower the redox potential of the environment and provides improved anaerobic conditions for the bacteria and enzyme. As an amino acid, cysteine is also an essential nitrogen source for certain bacteria. In the optimal media, due to its low concentration in the media and several other complex nitrogen sources being present, its role is more likely as a reducing agent. However, it is also a source of nitrogen for the bacteria. In terms of the reducing capability of cysteine, the thiol group is of most importance. Other thiol based reducing agents useful in fermentation, lyoprotection and cryoprotection include, without limitation, sodium thioglycolate, glutathione, sodium sulfide, and DTT (dithiothreitol).

In one embodiment, the highly bsh active bacteria are free bacteria. The term "free bacteria" as used herein refers to bacteria that are not immobilized in a polymer or encapsulated by artificial cell microencapsulation.

In another embodiment, the highly bsh active bacteria are contained or immobilized in a polymer, optionally a natural polymer. Natural polymers include, without limitation, alginate, chitosan, agarose, pectin, agaropectin, genipin, and cellulose. In an embodiment, the highly bsh active bacteria are immobilized on a film.

In yet another embodiment, the highly bsh active bacteria are encapsulated. Encapsulation is a term used to include the methods of macroencapsulation, microencapsulation and nanoencapsulation. The terms microencapsulation and nanoencapsulation refer to a subclass of encapsulation, where small, micro- or nano-encapsulated capsules are produced. Encapsulation and microencapsulation techniques are known in the art. Microcapsules are small spherical containers or coated tissues in the 1-999 µm range and nanocapsules range from 1-999 nm, whereas macrocapsules are larger flat-sheet or hollow-fiber membraned vessels. Macro-, micro- and nano-capsules must contain a cellular environment that is able to support cellular metabolism and proliferation, as the cells they accommodate provide the capsule functionality.

Artificial cell microencapsulation or nanoencapsulation is a technique used to encapsulate biologically active materials in specialized ultra thin semi-permeable polymer membranes (see e.g., Chang and Prakash, 1997; Chang, 1964). Methods for preparing artificial cells have been well documented in the pertinent art. Artificial cell membranes are optionally selected or designed for each specific therapeutic device by one of skill in the art, because one may engineer several different membranes for artificial cell preparations with required membrane properties for a desired application. The use of different membranes allows for variation in permeability, mass transfer, mechanical stability, buffering capability, biocompatibility, and other characteristics. A balance has to be maintained among the physical properties of capsule membranes so as to support the entrapped cell's survival.

Microcapsules can be prepared for the bacteria of the invention using techniques as in US Publication No. 2007-0116671 to Prakash and Jones, which is incorporated herein by reference.

The mass transport properties of a membrane are critical since the influx rate of molecules, essential for cell survival, and the outflow rate of metabolic waste ultimately determines the viability of entrapped cells. Any barriers can be potentially applied to enzyme applications. Ordinarily the desired capsule permeability is determined by the molecular weight cut-off (MWCO), and is application dependent. The MWCO is the maximum molecular weight of a molecule that is allowed passage through the pores of the capsule membrane (Uludag et al. (2000) *Adv. Drug Deliv. Rev.* 42:29-64). For transplantation, the MWCO must be high enough to allow passage of nutrients, but low enough to reject antibodies and other immune system molecules. The MWCO range is optionally 3000 D to 950,000 D (Chang and Prakash, 1998). The MWCO of orally delivered microcapsules must allow for the passage of unwanted metabolites from the plasma into the microcapsule, and then must either facilitate the subsequent removal of the altered molecule or provide for its storage (Uludag et al., 2000). For cells of the present disclosure that are to be administered orally, one optionally uses a retainer that allows passage of nutrients, but blocks antibodies and other immune molecules, for example a semi-permeable membrane having a MWCO 3000 D to 950,000 D (Chang and Prakash, 1998). Alternatively, the lower end of the range may be about: 2000 D, 4000 D, 5000 D or 10,000 D and the higher end of the range may be about: 900,000 D, 750,000 D or 500,000 D.

The most common type of membrane used for cell therapy is the single alginate based polymer membrane; however, several other substances may be used such as various proteins, polyhemoglobin, and lipids (Uludag et al., 2000; Prakash and Jones, 2002). Yet another approach for membrane composition is to use a biodegradable synthetic polymer such as polylactide, polyglycolic acid, and polyanhydride. Commonly used membranes include hollow fiber Membranes, alginate-polylysine-alginate (APA) membrane, cellulose nitrate, polyamide, lipid-complexed polymer, and lipid vesicles. Established and promising polymers for live cell encapsulation and enzyme encapsulation include alginate-polylysine-alginate (APA), alginate-polymethylene-co-guanidine-alginate (A-PMCG-A), hydroxymethylacrylate-methyl methacrylate (HEMA-MMA), Multilayered HEMA-MMA-MAA, polyacrylonitrilevinylchloride (PAN-PVC), acrylonitirle/sodium methallylsuflonate (AN-69), polyethylene glycol/poly pentamethylcyclopentasiloxane/polydimethylsiloxane (PEG/PD$_5$/PDMS), poly N,N-dimethyl acrylamide (PDMAAm), Siliceous encapsulates, and cellulose sulphate/sodium alginate/polymethylene-co-guanidine (CS/A/PMCG). Other materials that are useful include, without limitation, cellulose acetate phthalate, calcium alginate and k-carrageenan-Locust bean gum gel beads, gellan-xanthan beads, poly(lactide-co-glycolides), carageenan, starch polyanhydrides, starch polymethacrylates, polyamino acids, enteric coating polymers.

The design of a membrane, intended for use in oral live cell therapy, must take into consideration several primary factors so as to minimize microbial death and maximize therapeutic effectiveness. To assure their efficacy, artificially encapsulated cells intended for oral administration must be designed to protect their living cargo against both the acidic environment of the stomach and immunoglobulin released by the intestinal immune response.

A useful composition is the encapsulation of calcium alginate beads with poly-L-lysine (PLL) forming alginate-poly-L-lysine-alginate (APA) microcapsules. In the APA membrane microcapsule, alginate forms the core and matrix for the cell and PLL binds to the alginate core. Binding of PLL to alginate is the result of numerous long-chain alkyl-amino groups within PLL that extend from the polyamide backbone in a number of directions and interact with various alginate molecules, through electrostatic interactions. The resulting cross-linkage produces a stable complex membrane that reduces the porosity of the alginate membrane and forms an immunoprotective barrier.

Alternatively, Alginate/Poly-l-lysine/Pectin/Poly-l-lysine/Alginate (APPPA), Alginate/Poly-l-lysine/Pectin/Poly-l-lysine/Pectin (APPPP), and Alginate/Poly-L-lysine/Chitosan/Poly-l-lysine/Alginate (APCPA) membranes are used for encapsulation. These multi-layer membrane compositions perform well in GI stability tests, providing for increased resistance to complete dissolution in water, dilute acids and base, as well as in the presence of ion chelators, while allowing for more precise control over membrane permeability.

There are various methods available for preparing artificial cells containing live cells for therapy. For example, for preparation of the classic alginate-polylysine-alginate (APA) membrane, the live cells, such as bacterial cells, are suspended in a matrix of the natural polymer alginate (1.5%). The viscous polymer-bacterial suspension is passed through a 23-gauge needle using a syringe pump. Sterile compressed air, passed through a 16-gauge coaxial needle, is then used to shear the droplets coming out of the tip of the 23-gauge needle. The droplets are allowed to gel for 15 minutes in a gently stirred ice-cold solution of solidifying chemicals, such as $CaCl_2$ (1.4%). After gelation in the $CaCl_2$, the beads are then washed with HEPES (0.05% in HEPES, pH 7.20), coated with polylysine (0.1% for 10 min) and washed again in HEPES (0.05% in HEPES, pH 7.20). The resultant capsules are then coated by reaction with alginate (0.1% for 10 min) and washed with appropriate chemicals to dissolve their inner core content. For this step a 3.00% citrate bath (3.00% in 1:1 HEPES-buffer saline, pH 7.20) is often used. The microcapsules formed can then be stored at 4° C. in minimal solution (10% cell nutrient to 90% water).

Accordingly, in one embodiment, the highly bsh active bacteria are encapsulated in polymeric semi permeable microcapsules (1-999 µm) or nanocapsules (1-999 nm). In one embodiment, polymeric semi permeable microcapsules or nanocapsule comprise Alginate/Poly-l-lysine/Alginate (APA), Alginate/Chitosan/Alginate (ACA) or Alginate/Genipin/Alginate (AGA) membranes. In another embodiment, the microcapsule or nanocapsule comprises Alginate/Poly-l-lysine/Pectin/Poly-l-lysine/Alginate (APPPA), Alginate/Poly-l-lysine/Pectin/Poly-l-lysine/Pectin (APPPP), Alginate/Poly-L-lysine/Chitosan/Poly-l-lysine/Alginate (APCPA), alginate-polymethylene-co-guanidine-alginate (A-PMCG-A), hydroxymethylacrylate-methyl methacrylate (HEMA-MMA), Multilayered HEMA-MMA-MAA, polyacrylonitrilevinylchloride (PAN-PVC), acrylonitirle/sodium methallylsuflonate (AN-69), polyethylene glycol/poly pentamethylcyclopentasiloxane/polydimethylsiloxane (PEG/PD5/PDMS) or poly N,N-dimethyl acrylamide (PDMAAm) membranes. In yet another embodiment, the microcapsule or nanocapsule comprises hollow fiber, cellulose nitrate, polyamide, lipid-complexed polymer, a lipid vesicle a siliceous encapsulate, cellulose sulphate/sodium alginate/polymethylene-co-guanidine (CS/NPMCG), cellulose acetate phthalate, calcium alginate, k-carrageenan-Locust bean gum gel beads, gellan-xanthan beads, poly(lactide-co-glycolides), carageenan, starch polyanhydrides, starch polymethacrylates, polyamino acids or enteric coating polymers.

In a further embodiment, the polymeric microcapsules or nanocapsules are resistant to gastro-intestinal conditions, such as pH 1-8 and/or bile [1-30 mmol]).

The oral compositions disclosed herein are optionally lyophilized, heat dried, or spray dried. Alternatively, the oral compositions are optionally prepared wet.

In an embodiment, the oral compositions described herein are lyophilized with lyoprotectants to ensure viability and improved bsh activity over time. Typical lyoprotectants include, without limitation, a final concentration of 0.2% to 10% maltodextrin and 0.05% to 0.33% yeast extract or 0.05-10%, optionally 0.05-2.5% inulin and 0.05 to 0.33% yeast extract. In one embodiment, the lyoprotectants comprise a final concentration of 2-4% maltodextrin and 0.1% yeast extract, 0.3% inulin and 0.1% yeast extract, or 0.05-10%, optionally 0.3% inulin. In another embodiment, the lyoprotectants comprise 0.2% to 10%, optionally 2-4%, maltodextrin and 0.01% to 0.1%, optionally 0.025 to 0.05%, cysteine. In yet another embodiment, the lyoprotectants comprise 0.2% to 10% maltodextrin, 0.01 to 0.1% cysteine and 0.05% to 0.33% yeast extract. In yet a further embodiment, the lyoprotectants comprise 0.05% to 10% inulin and 0.01 to 0.1% cysteine.

In another embodiment, the oral compositions described herein are stored in liquid to ensure viability and improved bsh activity. Typical liquid storage conditions include, without limitation, a final concentration of preservative solution comprising 2.5-10% growth media (as described herein), 50-99.99% yogurt or other fermented milk, 50-99.99% culture supernatant or 5% MRS solution.

In yet another embodiment, the oral compositions described herein are flash frozen to ensure viability and improved bsh activity. Typical flash freezing conditions include, without limitation, a final concentration of cryoprotectant solution comprising 0.2-10% maltodextrin, optionally 1-3%, maltodextrin and 0.05 to 0.33% yeast extract, optionally 0.1-0.2% yeast extract, 0.05 to 10% inulin, optionally at least 0.2% inulin, 0.5M Trehalose, 0.5M sucrose or fructose, 0.5M lactose, 0.5M maltose or 50-99.99%, optionally 50% spent media. In another embodiment, the oral composition is flash frozen in a final cryoprotectant solution comprising 0.2 to 10%, optionally 2-4% maltodextrin, 0.01 to 0.1%, optionally 0.025 to 0.05%, cysteine and optionally, 0.05 to 0.33% yeast extract. In yet a further embodiment, the oral composition is flash frozen in a final cryoprotectant solution comprising 0.05% to 10% inulin and 0.01 to 0.1% cysteine.

The term "carrier" as used herein refers to an acceptable carrier that facilitates administration to the subject. For example, an acceptable carrier that facilitates oral administration includes, without limitation, a supplement, food product, beverage, functional food or nutraceutical, or excipient. "Nutraceutical" means a product isolated or purified from foods (or sources used to make food, such as plants, animals or other organisms) that is thought to have a health benefit, such as a medicinal, physiological or prophylactic effect. "Functional Food Product" means it is food, is consumed as part of a diet and has health benefits, such as medicinal, physiological or prophylactic benefits beyond basic nutritional function of supplying nutrients.

In another embodiment, the carrier comprises a capsule, pill, gel capsule, liquid, or dissolvable film.

The oral compositions disclosed herein for reducing serum cholesterol, serum lipids, body fat, or atherogenic index or for prophylaxis or treatment of atherosclerosis, cardiovascular or cerebrovascular diseases optionally further comprise other agents or therapeutics for such indications. Accordingly, in one embodiment, the oral composition further comprises a triglyceride lowering agent, optionally, squalene synthase inhibitors, microsomal triglyceride transfer protein inhibitors, statins, bile acid sequestrants, cholesterol absorption inhibitors, fibrates and other PPAR alpha agonists, dual PPAR agonists, lipase inhibitors, protein tyrosine phosphatase 1B inhibitors, pancreatic peptide $YY_{3-36}$, recombinant and other cannabinoid receptor antagonists or 5-HT2c agonists, such as lorcaserin. In another embodiment, the composition further comprises an agent for increasing HDL or limiting HDL decrease, optionally, statins, bile acid sequestrants, cholesterol absorption inhibitors, fibrates and other PPAR alpha agonists, dual PPAR agonists, lipase inhibitors, protein tyrosine phosphatase 1B inhibitors, pancreatic peptide $YY_{3-36}$, recombinant and other cannabinoid receptor antagonists, or 5-HT2c agonists, such as lorcaserin. In yet another embodiment, the oral composition further comprises a cholesterol lowering agent, optionally, a bile acid sequestrant (BAS), a statin, ezetimibe, alpha-Linoleitic acid, omega-3,6,9, eicosapentaenoic acid (EPA), docosahexaenoic acid (DHA), fibrates, soluble fibre, polyphenol, gama-oryzanol hesperetin metabolite, phytochemical, other probiotic, psyllium, phytosterol, phytostanol, vitamin, antioxidant or antibiotic. The statin may be selected from the group consisting of Lovastatin, Pravastatin, Zocor, Fluvastatin, Mevastatin, Pitavastatin, Cerivastatin, Simvastatin, Rosuvastatin and Atorvastatin. The BAS may be colestyramine, colestipol or colesevelam. The fibrate may be clofibrate, bezafibrate, gemfibrozil or fenofibrate. In a further embodiment, the oral composition further comprises an agent for preserving bsh activity, optionally, inulin, trealose, maltodextran, yeast extract, polyethylene glycol, glycerol, lipid, emulsified fat, a dairy product, glucose, fructose, sucrose, a poly sugar, anhydrobiosis, a polycosanol, polyethlylene glycol (PEG), a plant sterol, a plant stanol, or an omega fatty acid. The polycosanol may be octacosanol, triacontanol, behenyl alcohol, lignoceryl alcohol, ceryl alcohol, 1-heptacosanol, 1-nonacosanol, 1-dotriacontanol, or geddyl alcohol. In yet a further embodiment, the oral composition further comprises an agent for modulating adipokines or hormones of obesity, optionally, leptin, ghrelin, resistin, adiponectin, chemerin, Il-6, visfatin, retinol binding protein 4 or plasminogen activator inhibitor-1. In yet another further embodiment, the oral composition further comprises a hypoglycemic agent, optionally, Metformin, Rosiglitazone, Pioglitazone, Glyburide, Gliclazide, Glimepiride, Glipizidebile Glibenclamide, Acarbose, Miglitol, Voglibose, Sitagliptin, Nateglinide, Repaglinide, Mitiglinide, Alogliptin, Saxagliptin, Vildagliptin and Dapagliflozin. In an even further embodiment, the oral composition further comprises a therapeutic for reducing the pro-inflammatory cytokines IL-1α/β, IL-2, IL-15, IL-3, IL-6, IL-8, IL-12, IL-17, IFN-gamma, TNF-alpha, or for increasing the level of the anti-inflammatory cytokines IL-1ra, IL-9, IL-10, IL-11.

In yet another embodiment, the oral composition further comprises vitamin B12. In a further embodiment, the oral composition further comprises conjugated linoleic acid (CLA). In yet a further embodiment, the oral composition further comprises reuterin and/or reutericyclin.

Methods and Uses

The disclosure includes methods and uses of the oral compositions disclosed herein. In one embodiment, there is provided a method of therapy comprising administration of an oral composition disclosed herein to an animal in need thereof. Also provided is a use of an oral composition disclosed herein for therapy of an animal. Further provided is a use of an oral composition disclosed herein in the preparation of a medicament for therapy. Also provided is the oral composition disclosed herein for use in therapy.

The compositions described herein are useful for lowering serum cholesterol of an animal in need thereof. Accordingly, in one aspect, the present disclosure provides a method of lowering serum cholesterol in an animal in need thereof comprising administering an oral composition disclosed herein. There is also provided a use of an oral composition disclosed herein for lowering serum cholesterol in an animal in need thereof. Also provided is a use of an oral composition disclosed herein in the preparation of a medicament for lowering serum cholesterol in an animal in need thereof. Further provided is an oral composition disclosed herein for use in lowering serum cholesterol in an animal in need thereof. In one embodiment, a bile acid lowering amount of the oral composition is used.

In one embodiment, the animal in need thereof has a disease or disorder characterized by increased cholesterol accumulation in serum and/or tissue causing pathology or having excessive cholesterol as a risk factor. Cholesterol disorders include familial hypercholesterolemia or inherited cholesterol disorder (ICD), defects in the gene products of cholesterol metabolism e.g. 7-alpha-hydroxylase, and various forms of xanthomas. Increased levels of serum cholesterol may indicate atherosclerosis, biliary cirrhosis, familial hyperlipidemias, high-cholesterol diet, hypothyroidism, myocardial infarction, nephritic syndrome and uncontrolled diabetes. "Excessive cholesterol" means outside the typical (normal) cholesterol range. Typical cholesterol level is less than 200 mg/dL. Borderline High is 200-239 mg/dL and anything over 240 mg/dL is high. The National Cholesterol Education Program NCEP III report on cholesterol includes "Full Report" and a "Drug Therapy" section. This provides a review of examples of cholesterol management by statins, bile acid sequestrants, diet, etc. and it relates to cholesterol levels and risk factors (eg. see Tables IV.1-1 VI.1-1; VI.1-2, VI.1-3). The compositions described herein are similar to bile acid sequestrants in that they reduce bile levels. The NCEP report provides guidance on use of pharmaceutical therapy in relation to the presence of other risk factors. There are two types of cholesterol, HDL cholesterol (sometimes called good cholesterol) and LDL cholesterol (sometimes called bad cholesterol). "Excessive cholesterol" may also be determined with respect to LDL. For example, drug therapy is optionally considered for individuals with multiple risk factors (2 or more) when LDL cholesterol is: >100 mg/dL (eg. with a goal to reduce LDL cholesterol to <100 mg/dL), at least 130 mg/dL (eg. with a goal to reduce LDL cholesterol to less than 130 mg/dL), at least 160 mg/dL (eg. with a goal to reduce LDL cholesterol to less than 130 mg/dL). Furthermore, drug therapy is also optionally considered for individuals with 0-1 risk factors when LDL cholesterol is at least 190 mg/dL (eg. with a goal to reduce LDL cholesterol to less than 160 mg/dL). Normal values tend to increase with age, and premenopausal women have somewhat lower levels than men of the same age.

In another embodiment, the present disclosure provides a method for increasing or limiting the reduction of serum high density lipoproteins (HDL-C) of an animal comprising administering an oral composition disclosed herein. Also provided is use of an oral composition disclosed herein for increasing or limiting the reduction of serum HDL-C in an animal in need thereof. Further provided is use of an oral composition disclosed herein in the preparation of a medicament for increasing or limiting the reduction of serum HDL-C in an animal in need thereof. Also provided is an oral composition disclosed herein for use in increasing or limiting the reduction of serum HDL-C in an animal in need thereof.

In a further embodiment, the methods the present disclosure provides a method for decreasing serum triglycerides of an animal comprising administering an oral composition disclosed herein. Also provided is use of an oral composition disclosed herein for decreasing serum triglycerides in an animal in need thereof. Further provided is use of an oral composition disclosed herein in the preparation of a medicament for decreasing serum triglycerides in an animal in need thereof. Also provided is an oral composition disclosed herein for decreasing serum triglycerides in an animal in need thereof.

In yet a further embodiment, the present disclosure provides a method for reducing atherosclerotic risk factors of an animal comprising administering an oral composition disclosed herein. Also provided is use of an oral composition disclosed herein for reducing atherosclerotic risk factors in an animal in need thereof. Further provided is use of an oral composition disclosed herein in the preparation of a medicament for reducing atherosclerotic risk factors in an animal in need thereof. Also provided is an oral composition disclosed herein for reducing atherosclerotic risk factors in an animal in need thereof. Atherosclerotic risk factors, include, without limitation serum homocystine, fibrinogen, C-reactive protein, lipoprotein(a), uric acid, matrix metallopeptidase 9 (MMP-9), plasminogen activator inhibitor-1 (PAI-1) or its antigen, tissue plasminogen activator (tPA), TNF alpha, IL-6, P-selectin, monocyte chemotactic protein-1 (MCP-1), soluble CD40 ligand (sCD40L), intercellular adhesion molecule 1 (ICAM-1), myeloperoxidase (MPO), adiponectin, leptin, lipoprotein-associated phospholipase A and insulin.

In yet another embodiment, the present disclosure provides a method for producing and delivering vitamin B12 to an animal comprising administering an oral composition disclosed herein. Also provided is use of an oral composition disclosed herein for producing and delivering vitamin B12 in an animal in need thereof. Further provided is use of an oral composition disclosed herein in the preparation of a medicament for producing and delivering vitamin B12 in an animal in need thereof. Also provided is an oral composition disclosed herein for producing and delivering vitamin B12 in an animal in need thereof.

In a further embodiment, the present disclosure provides a method for producing and delivering conjugated linoleic acid (CLA) to an animal comprising administering an oral composition disclosed herein. Also provided is use of an oral composition disclosed herein for producing and delivering conjugated linoleic acid (CLA) in an animal in need thereof. Further provided is use of an oral composition disclosed herein in the preparation of a medicament for producing and delivering conjugated linoleic acid (CLA) in an animal in need thereof. Also provided is an oral composition disclosed herein for producing and delivering conjugated linoleic acid (CLA) in an animal in need thereof.

In yet a further embodiment, the present disclosure provides a method of producing and delivering reuterin and reutericyclin to an animal comprising administering an oral composition disclosed herein. Also provided is use of an oral composition disclosed herein for producing and delivering reuterin and reutericyclin in an animal in need thereof. Further provided is use of an oral composition disclosed herein in the preparation of a medicament for producing and delivering reuterin and reutericyclin in an animal in need thereof. Also provided is an oral composition disclosed herein for producing and delivering reuterin and reutericyclin in an animal in need thereof.

The oral compositions described herein are also useful for decreasing serum triglycerides in an animal in need thereof. Accordingly, in one aspect, the present disclosure provides a method of decreasing serum triglycerides in an animal in need thereof comprising administering an oral composition disclosed herein. There is also provided a use of an oral composition disclosed herein for decreasing serum triglycerides in an animal in need thereof. Also provided is a use of an oral composition disclosed herein in the preparation of a medicament for decreasing serum triglycerides in an animal in need thereof. Further provided is an oral composition disclosed herein for use in decreasing serum triglycerides in an animal in need thereof. In one embodiment, a bile acid lowering amount of the oral composition is used.

In another aspect, the present disclosure provides a method for reducing the atherogenic index of an animal, comprising administering to the animal an oral composition of the disclosure. Also provided is a use of a composition of the disclosure for reducing the atherogenic index of an animal. Also provided is a use of an oral composition of the disclosure in the preparation of a medicament for reducing the atherogenic index of an animal. Further provided is an oral composition of the disclosure for use in reducing the atherogenic index of an animal. Atherogenic index is calculated using at least one of the equations shown in Table 1. In one embodiment, a bile acid lowering amount of the oral composition is used.

In yet another aspect, the disclosure provides a method for prophylaxis or treatment of atherosclerosis or a degenerative disorder caused by atherosclerosis in an animal comprising administering to the animal an oral composition of the disclosure. Also provided is a use of an oral composition of the disclosure for prophylaxis or treatment of atherosclerosis or a degenerative disorder caused by atherosclerosis. Also provided is a use of an oral composition of the disclosure in the preparation of a medicament for prophylaxis or treatment of atherosclerosis or a degenerative disorder caused by atherosclerosis. Further provided is an oral composition of the disclosure for use in the prophylaxis or treatment of atherosclerosis or a degenerative disorder caused by atherosclerosis. Degenerative disorders include, without limitation cerebrovascular disease, stroke, vascular disease, coronary artery disease, myocardial infarction, thrombosis, angina, unstable angina, intermittent claudication, transient ischemic attack, or renal failure. In one embodiment, a bile acid lowering amount of the oral composition is used.

The term "prophylaxis or treatment of" refers to decreasing the likelihood of a condition or ameliorating a condition.

In a further aspect, the disclosure provides a method for lowering total body fat or treating obesity or pre-obesity in an animal, comprising administering to the animal an oral composition of the disclosure. Also provided is a use of an oral composition of the disclosure for lowering total body fat or treating obesity or pre-obesity in an animal. Also provided is a use of an oral composition of the disclosure in the preparation of a medicament for lowering total body fat or treating obesity or pre-obesity in an animal. Further provided is an oral composition of the disclosure for use in lowering total body fat or treating obesity or pre-obesity in an animal. The term "obesity" as used herein refers to a disease, medical condition or disorder and is defined as a body mass index (BMI)>30. A BMI of 25-30 is pre-obese. In one embodiment, a bile acid lowering amount of the oral composition is used.

In yet a further aspect, the disclosure provides a method for prophylaxis or treatment of a metabolic disease or disorder in an animal comprising administering to the animal an oral composition of the disclosure. Also provided is a use of an oral composition of the disclosure for prophylaxis or treatment of a metabolic disease or disorder in an animal. Also provided is a use of an oral composition of the disclosure in the preparation of a medicament for prophylaxis or treatment of a metabolic disease or disorder in an animal. Further provided is an oral composition of the disclosure for use in the prophylaxis or treatment of a metabolic disease or disorder in an animal. Metabolic diseases and disorders include, without limitation, hyperlipidemia, hyperglycemia, hyperlipoproteinemia, impaired glucose tolerance (IGT), insulin resistance, pre-diabetes, type I diabetes, type II diabetes, and metabolic syndrome. In one embodiment, a bile acid lowering amount of the oral composition is used.

In another aspect, the disclosure provides a method for prophylaxis or treatment of a liver disease or disorder associated with high serum or hepatic lipid and triglyceride concentrations, hepatic inflammation, non-alcoholic fatty liver disease (NAFLD), alcoholic fatty liver disease (AFLD), non-alcoholic steatohepatitis (NASH), liver cirrhosis, liver steatosis, liver fibrosis, abnormally high serum ALT, AST, GGT, or Alk-P levels, Epstein-Barr virus, hepatitis, autoimmune hepatitis, hepatic granulomatus disease, cholangitis, hepatocellular cancer, cholangiocarcinoma, metabolic liver disease in an animal, comprising administering to the animal an oral composition of the disclosure. Also provided is a use of an oral composition of the disclosure for prophylaxis or treatment of a liver disease or disorder associated with high serum or hepatic lipid and triglyceride concentrations, hepatic inflammation, non-alcoholic fatty liver disease (NAFLD), alcoholic fatty liver disease (AFLD), non-alcoholic steatohepatitis (NASH), liver cirrhosis, liver steatosis, liver fibrosis, abnormally high serum ALT, AST, GGT, or Alk-P levels, Epstein-Barr virus, hepatitis, autoimmune hepatitis, hepatic granulomatus disease, cholangitis, hepatocellular cancer, cholangiocarcinoma, metabolic liver disease in an animal. Also provided is a use of an oral composition of the disclosure in the preparation of a medicament for prophylaxis or treatment of a liver disease or disorder associated with high serum or hepatic lipid and triglyceride concentrations, hepatic inflammation, non-alcoholic fatty liver disease (NAFLD), alcoholic fatty liver disease (AFLD), non-alcoholic steatohepatitis (NASH), liver cirrhosis, liver steatosis, liver fibrosis, abnormally high serum ALT, AST, GGT, or Alk-P levels, Epstein-Barr virus, hepatitis, autoimmune hepatitis, hepatic granulomatus disease, cholangitis, hepatocellular cancer, cholangiocarcinoma, metabolic liver disease in an animal. Further provided is an oral composition of the disclosure for use in the prophylaxis or treatment of a liver disease or disorder associated with high serum or hepatic lipid and triglyceride concentrations, hepatic inflammation, non-alcoholic fatty liver disease (NAFLD), alcoholic fatty liver disease (AFLD), non-alcoholic steatohepatitis (NASH), liver cirrhosis, liver steatosis, liver fibrosis, abnormally high serum ALT, AST, GGT, or Alk-P levels, Epstein-Barr virus, hepatitis, autoimmune hepatitis, hepatic granulomatus disease, cholangitis, hepatocellular cancer, cholangiocarcinoma, metabolic liver disease in an animal. In one embodiment, a bile acid lowering amount of the oral composition is used.

Other agents or therapeutics can be coadministered or used in combination with the oral compositions disclosed herein. Accordingly, in an embodiment, the methods and uses disclosed herein further comprise administering a triglyceride lowering agent, optionally, squalene synthase inhibitors, microsomal triglyceride transfer protein inhibitors, statins, bile acid sequestrants, cholesterol absorption inhibitors, fibrates and other PPAR alpha agonists, dual PPAR agonists, lipase inhibitors, protein tyrosine phosphatase 1B inhibitors, pancreatic peptide $YY_{3-36}$, recombinant and other cannabinoid receptor antagonists or 5-HT2c agonists, such as lorcaserin. In another embodiment, the methods and uses disclosed herein further comprise administering an agent for increasing HDL or limiting HDL decrease, optionally, statins, bile acid sequestrants, cholesterol absorption inhibitors, fibrates and other PPAR alpha agonists, dual PPAR agonists, lipase inhibitors, protein tyrosine phosphatase 1B inhibitors, pancreatic peptide $YY_{3-36}$, recombinant and other cannabinoid receptor antagonists, or 5-HT2c agonists, such as lorcaserin. In yet another embodiment, the methods and uses disclosed herein further comprise administering a cholesterol lowering agent, optionally, a bile acid sequestrant (BAS), a statin, ezetimibe, alpha-Linoleitic acid, omega-3,6,9, eicosapentaenoic acid (EPA), docosahexaenoic acid (DHA), fibrates, soluble fibre, polyphenol, gama-oryzanol hesperetin metabolite, phytochemical, other probiotic, psyllium, phytosterol, phytostanol, vitamin, antioxidant or antibiotic. The statins, include, without limitation, Lovastatin, Pravastatin, Zocor, Fluvastatin, Mevastatin, Pitavastatin, Cerivastatin, Simvastatin, Rosuvastatin and Atorvastatin. The BAS include, without limitation colestyramine, colestipol and colesevelam. The fibrates include, without limitation, clofibrate, bezafibrate, gemfibrozil and fenofibrate. In yet another embodiment, the methods and uses disclosed herein further comprise administering an agent for preserving bsh activity, optionally, inulin, trealose, maltodextran, yeast extract, polyethylene glycol, glycerol, lipid, emulsified fat, a dairy product, glucose, fructose, sucrose, a poly sugar, anhydrobiosis, a polycosanol, polyethlylene glycol (PEG), a plant sterol, a plant stanol, or an omega fatty acid. The polycosanol includes, without limitation, octacosanol, triacontanol, behenyl alcohol, lignoceryl alcohol, ceryl alcohol, 1-heptacosanol, 1-nonacosanol, 1-dotriacontanol, and geddyl alcohol. In a further embodiment, the methods and uses disclosed herein further comprise administering an agent for modulating adipokines or hormones of obesity, optionally, leptin, ghrelin, resistin, adiponectin, chemerin, Il-6, visfatin, retinol binding protein 4 or plasminogen activator inhibitor-1. In yet a further embodiment, the methods and uses disclosed herein further comprise administering a hypoglycemic agent, optionally, Metformin, Rosiglitazone, Pioglitazone, Glyburide, Gliclazide, Glimepiride, Glipizidebile Glibenclamide, Acarbose, Miglitol, Voglibose, Sitagliptin, Nateglinide, Repaglinide, Mitiglinide, Alogliptin, Saxagliptin, Vildagliptin and Dapagliflozin. In another embodiment, the methods and uses disclosed herein further comprise administering a therapeutic for reducing the pro-inflammatory cytokines IL-1α/β, IL-2, IL-15, IL-3, IL-6, IL-8, IL-12, IL-17, IFN-gamma, TNF-alpha, or for increasing the level of the anti-inflammatory cytokines IL-1ra, IL-9, IL-10, IL-11.

The term "animal" as used herein refers to any member of the animal kingdom, optionally, a mammal, such as a human.

Administration of an "effective amount" or "bile acid lowering amount" of the agents described herein is defined as an amount effective at dosages and for periods of time necessary to achieve the desired result. The effective amount of the highly bsh active bacterial composition is optionally adjusted according to factors such as the disease state, age, sex, and weight of the animal. Dosage regimens are readily adjusted to provide the optimum therapeutic response. For example, several divided doses may be administered daily or the dose may be proportionally reduced as indicated by the exigencies of the therapeutic situation. In one embodiment, the compositions may be administered or used 1 to 4 times per day.

The compositions can be prepared by known methods for the preparation of pharmaceutically acceptable compositions which can be administered to patients, and such that an effective quantity of the cell is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA 2003—20$^{th}$ Edition) and in The United States Pharmacopeia: The National Formulary (USP 24 NF19) published in 1999).

Processes for Growing and Preparing Bacteria

Also provided herein are processes for preparing a highly bsh active bacteria comprising growing bsh-producing bacteria under fermentation conditions that support development of high bsh activity. Suitable fermentation conditions have been described in the compositions section above. For example, the fermentation conditions optionally comprise a carbon source, a nitrogen source, a pH of 4 to 7 and a harvest time of 6 to 24 hours, optionally 8-16 hours. In one embodiment, the carbon source is a sugar that optionally comprises maltose, sucrose, dextrin, a combination of sorbitol and glucose or a combination of inulin and glucose. In a particular embodiment, the carbon source is maltose. In another embodiment, the nitrogen source comprises (i) yeast extract and malt extract, yeast extract and beef extract, or casein hydrolysate and malt extract; and (ii) peptone or tryptone. In a particular embodiment, the peptone is peptone no. 3. Typical concentrations of carbon and nitrogen sources are as described in the compositions section above. In another embodiment, the fermentation conditions further comprise a reducing agent, such as cysteine.

In a further embodiment, the process further comprises lyophilizing the free or microencapsulated bacterial compositions with lyoprotectants as described herein. In one embodiment, the lyoprotectants comprise a final concentration of 0.2% to 10% maltodextrin and 0.05% to 0.33% yeast extract or 0.05-10%, optionally 0.05 to 2.5% inulin and 0.05 to 0.33% yeast extract. In one embodiment, the lyoprotectants comprise a final concentration of 2-4% maltodextrin and 0.1% yeast extract, 0.3% inulin and 0.1% yeast extract, or 0.05-10%, optionally 0.3%, inulin. In another embodiment, the lyoprotectants comprise a final concentration of 0.2% to 10% maltodextrin and 0.01% to 0.1% cysteine. In yet another embodiment, the lyoprotectants comprise 0.2% to 10% maltodextrin, 0.01 to 0.1% cysteine and 0.05% to 0.33% yeast extract. In yet another embodiment, the lyoprotectants comprise 0.05% to 10% inulin and 0.01 to 0.1% cysteine. Maltodextrin concentrations are higher when lyophilizing free cells (about 7.5%) compared to microcapsules (about 1-2%). Cysteine concentrations are also higher when lyophilizing free cells as compared to microcapsules, due to the higher concentration of bacterial cells.

In an alternate embodiment, the process further comprises storing the highly bsh active free or microencapsulated bacterial composition under liquid storage conditions. In one embodiment, the liquid storage conditions comprise a final preservative solution comprising 2.5-10% growth media, 50-99.99% yogurt or other fermented milk, 50-99.99% culture supernatant or 5% MRS solution.

In yet another embodiment, the process further comprises flash freezing the free or microencapsulated composition in cryoprotectant solution as described herein. In one embodiment, the cryoprotectant solution comprises a final concentration of 0.2-10% maltodextrin, optionally 1-3%, maltodextrin and 0.05 to 0.33% yeast extract, optionally 0.1-0.2% yeast extract, 0.05 to 10% inulin, optionally at least 0.2% inulin, 0.5M Trehalose, 0.5M sucrose or fructose, 0.5M lactose, 0.5M maltose or 50-99.99%, optionally 50% spent media. In another embodiment, the cryoprotectant solution comprises a final concentration of 0.2 to 10% maltodextrin, 0.01 to 0.1% cysteine and optionally, 0.05 to 0.33% yeast extract. In yet a further embodiment, the cryoprotectant solution comprises a final concentration of 0.05% to 10% inulin and 0.01 to 0.1% cysteine. Flash freezing as used herein refers to subjecting the composition to temperatures below −80 degrees Celsius, for example, by subjecting the free or microencapsulated composition to liquid nitrogen such as at a temperature of −196 degrees Celsius, or freezing the composition at ultra low temperatures, such as −130 degrees Celsius, or using dry ice.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient.

The following non-limiting examples are illustrative of the present disclosure:

EXAMPLES

Figure 2:
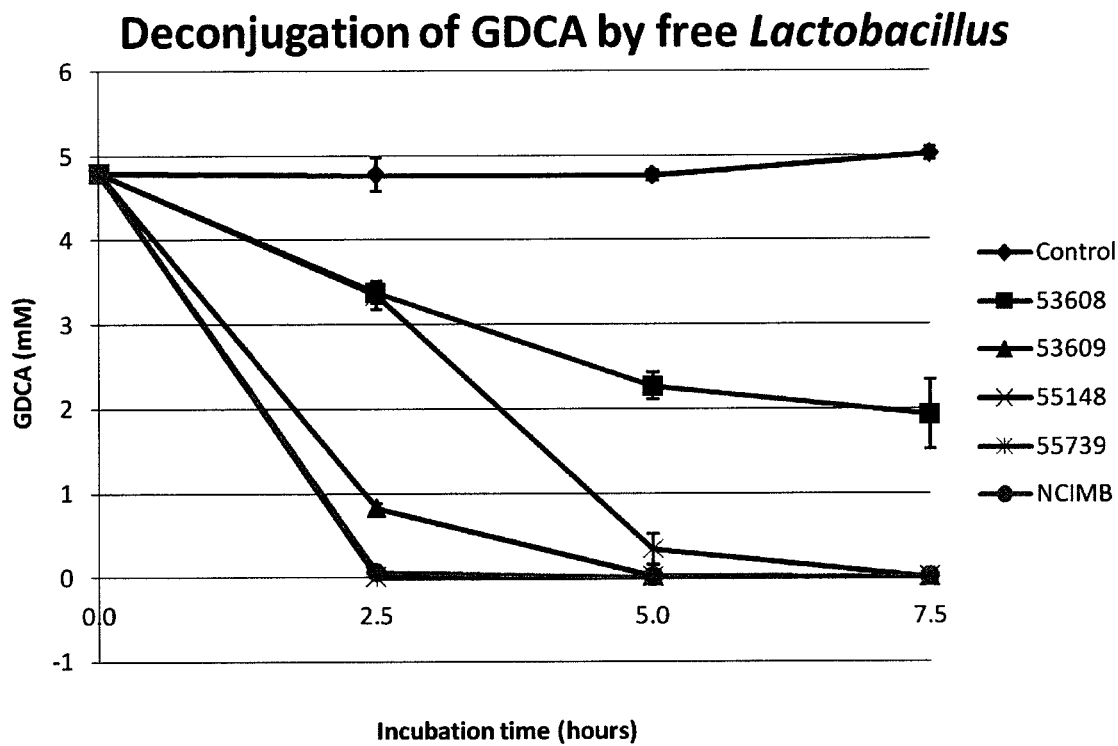
FIG. 2 shows deconjugation of GDCA by free *Lactobacillus reuteri* strains (ATCC 53608, ATCC 53609, ATCC 55148, ATCC 55739, and NCIMB 701359) over time. The experiment was performed in triplicate and error bars represent one standard deviation from the mean.

Deconjugation of TDCA and GDCA by Free *Lactobacillus reuteri* Strains (FIGS. 1 and 2)

Results

FIGS. 1 and 2 show the deconjugation of taurodeoxycholic acid and glycodeoxycholic acid, as measured by HPLC, in an in-vitro assay using 0.4 grams of free *Lactobacillus reuteri* (ATCC 53608, ATCC 53609, ATCC 55148, ATCC 55739, and NCIMB 701359) over time. The NCIMB 701359 and ATCC 55739 *Lactobacillus reuteri* strains have the highest bsh activity as measured by HPLC. One should take into consideration the limitations to the assay "resolution" (using 0.4 grams and sampling over 2.5 hours); however, these strains were still shown to be considerably more bsh active than the others tested in this experiment and as the level of GDCA is not measurable at 2.5 hours there is an even greater difference in bsh activity, as the substrate became limiting.

Materials and Methods

Bacteria and Culture Conditions

Four *Lactobacillus reuteri* strains obtained from ATCC (53609, 53608, 55148 and 55739) and NCIMB 701359 were cultivated in sterile de Man, Rogosa, Sharpe (MRS) broth at 37° C. for 20 hours. Grown cultures were isolated by centrifugation and collected bacteria cells were used in the following BSH assay.

Measurement of BSH Activity

To measure the BSH activity, collected bacteria were added into 100% MRS supplemented with a combination of sodium glycodeoxycholate and sodium taurodeoxycholate both at 5 mM (0.4 g bacteria cells/20 ml MRS supplemented with GDCA and TDCA). Bacteria were then incubated in the reaction broth anaerobically at 37° C. with minimal shaking (100 rpm), and supernatant was sampled at intervals of 2.5 hours and processed to determine the conjugated bile salt concentrations. Briefly, 500 µl samples were acidified with 5 ul of 6N HCl after removing bacteria cells by centrifugation at 10000 g for 3 min. The supernatants were then supplemented with 500 µl of Methanol containing 4 mM GCA (glycocholic acid) as internal standard. The samples were vortexed for 10 min and centrifuged at 1000 g for 15 min. The samples were filtered through 0.22 µM filter before being analyzed by HPLC. HPLC analysis of bile salts followed the procedure described by Jones et al. 2003.

Bile Salt HPLC Analysis

HPLC analysis of bile salts followed the procedure described by Jones et al. 2003. The analysis was performed on a reverse-phase C-18 column: LiChrosorb RP-18, 5 µm, 250×4.6 mm. The HPLC system comprised of two ProStar 210 solvent delivery modules, a ProStar 320 UV-VIS detector, a ProStar 410 autosampler and Galaxie Chromatography Data system (version 1.9.3.2). A mixture of methanol and 50 mM sodium acetate buffer adjusted to pH4.3 with o-phosphoric acid (70:30, v/v) was applied as mobile phase with a flow rate of 1.0 ml/min. The detector was set at 210 nm and all the measurements were performed at room temperature.

Figure 3:
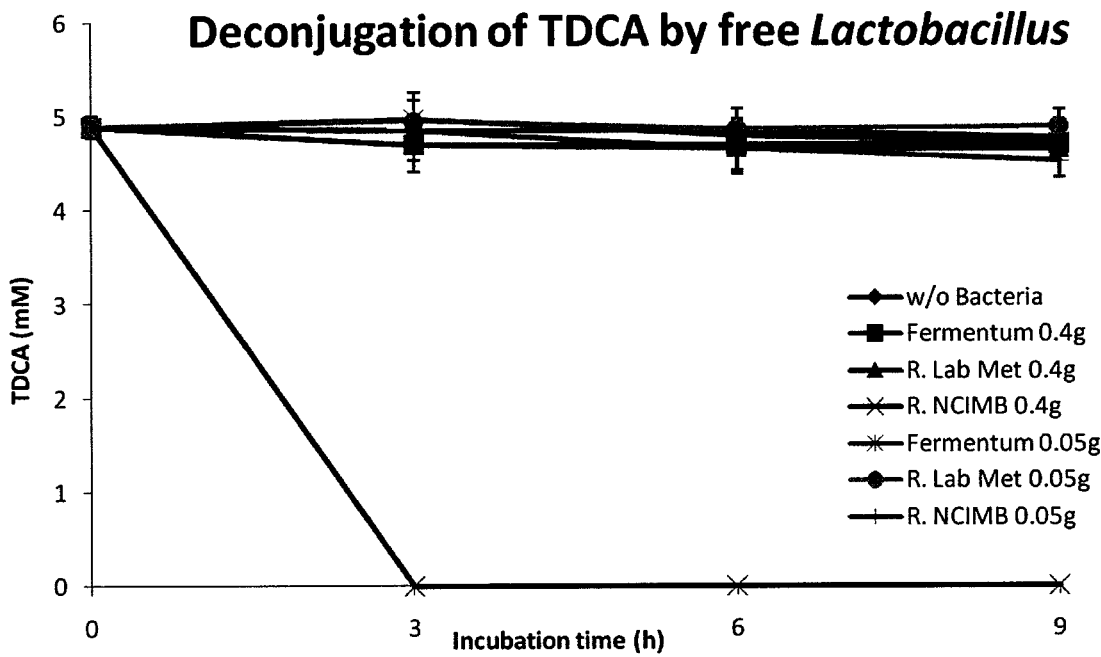
FIG. 3 shows deconjugation of TDCA by free *Lactobacillus reuteri* and *Lactobacillus fermentum* strains over time. The experiment was performed in triplicate and error bars represent one standard deviation from the mean.
Figure 4:
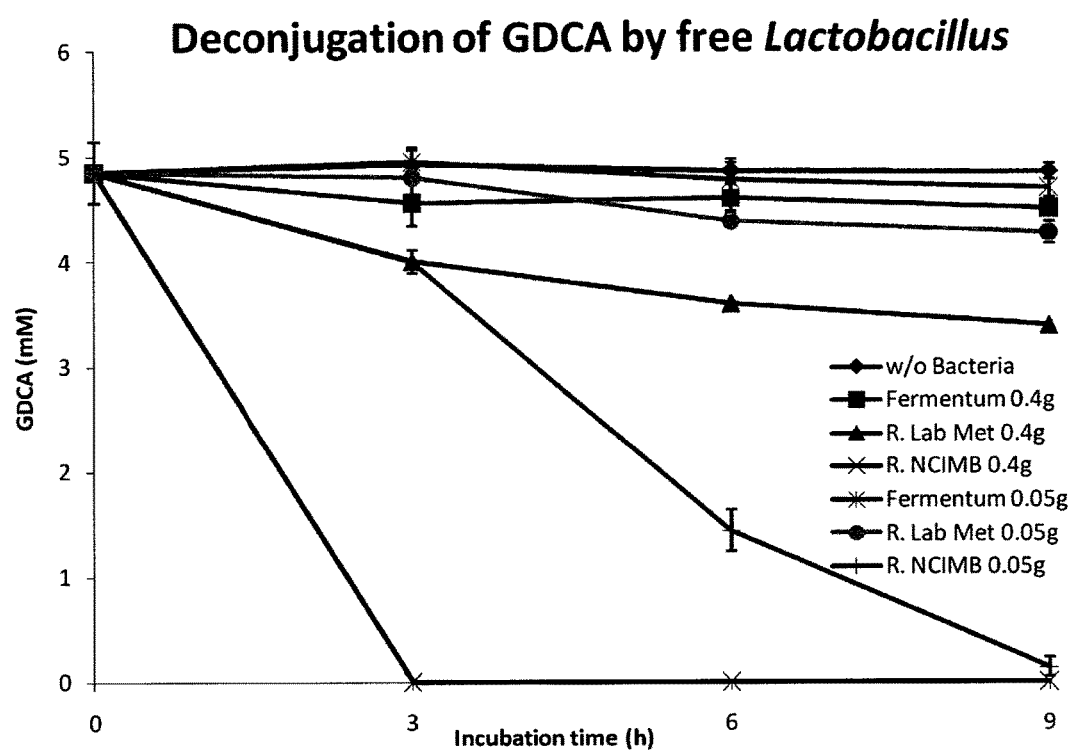
FIG. 4 shows deconjugation of GDCA by free *Lactobacillus reuteri* strains (LabMet, NCIMB 701359) and *Lactobacillus fermentum* (ATCC 11976) over time. The experiment was performed in triplicate and error bars represent one standard deviation from the mean.

Deconjugation of TDCA and GDCA by Free *Lactobacillus reuteri* and *Lactobacillus fermentum* (FIGS. 3 and 4)

Results

FIGS. 3 and 4 show the deconjugation of taurodeoxycholic acid and glycodeoxycholic acid as measured by HPLC in an in-vitro assay of free *Lactobacillus reuteri* (Lab Met, NCIMB 701359) and *Lactobacillus fermentum* (ATCC 11976) over time. *Lactobacillus reuteri* (NCIMB 701359) has a much greater bsh activity than *Lactobacillus reuteri* (LabMet) or *Lactobacillus fermentum* (ATCC 11976) and even a fraction (⅛th) of the quantity of *Lactobacillus reuteri* (NCIMB 701359) cells outperform *Lactobacillus reuteri* (LabMet) in-vitro.

Materials and Methods

Bacteria and Culture Conditions

The bacterial strains used in this study are *L. reuteri* (LabMet, NCIMB 701359) and *L. fermentum* (ATCC 11976). The bacteria were cultivated in sterile de Man, Rogosa, Sharpe (MRS) broth at 37° C. for 20 hours. Grown cultures were isolated by centrifugation and collected bacteria cells were used in the following BSH assay.

Measurement of BSH Activity

To measure the BSH activity, collected bacteria were added into 100% MRS supplemented with a combination of sodium glycocholate and sodium taurocholate at 5 mM (0.4 g or 0.05 g bacteria/20 ml MRS supplemented with GDCA and TDCA). Bacteria were then incubated anaerobically at 37° C., and supernatant was sampled at intervals of 3 hours and processed to determine the conjugated bile salt concentrations in the reaction tubes. Briefly, 500 μl samples were acidified with 5 μl of 6N HCl after removing bacteria cells by centrifugation at 10000 g for 3 min. The supernatants were then supplemented with 500 μl of Methanol containing 4 mM GCA (glycocholic acid) as internal standard. The samples were vortexed for 10 min and centrifuged at 1000 g for 15 min. The samples were filtered through 0.22 μM filter before being analyzed by HPLC. HPLC analysis of bile salts followed the procedure described by Jones et. al.

Bile Salt HPLC Analysis

HPLC analysis of bile salts followed the procedure described by Jones et al. 2003. The analysis was performed on a reverse-phase C-18 column: LiChrosorb RP-18, 5 μm, 250×4.6 mm. The HPLC system comprised of two ProStar 210 solvent delivery modules, a ProStar 320 UV-VIS detector, a ProStar 410 autosampler and Galaxie Chromatography Data system (version 1.9.3.2). A mixture of methanol and 50 mM sodium acetate buffer adjusted to pH4.3 with o-phosphoric acid (70:30, v/v) was applied as mobile phase with a flow rate of 1.0 ml/min. The detector was set at 210 nm and all the measurements were performed at room temperature.

Figure 5:
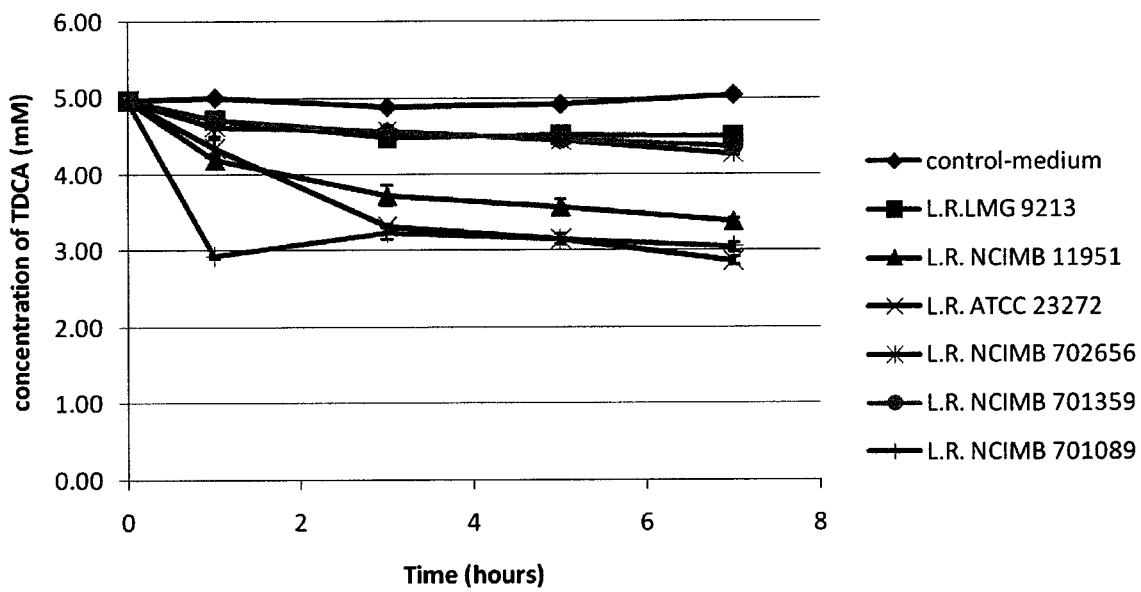
FIG. 5 shows deconjugation of TDCA by free *Lactobacillus reuteri* strains (LMG 9213, NCIMB 11951, ATCC 23272, NCIMB 702656, NCIMB 701359, and NCIMB 701089) over time. The experiment was performed in triplicate and error bars represent one standard deviation from the mean.
Figure 6:
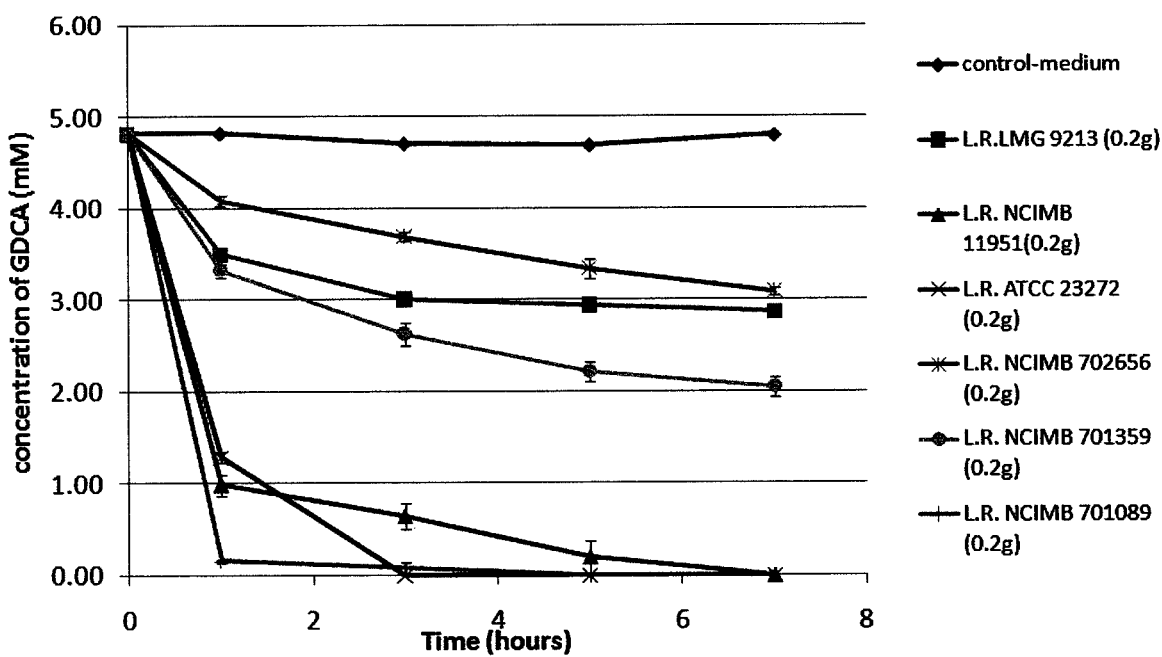
FIG. 6 shows deconjugation of GDCA by free *Lactobacillus reuteri* strains (LMG 9213, NCIMB 11951, ATCC 23272, NCIMB 702656, NCIMB 701359, and NCIMB 701089) over time. The experiment was performed in triplicate and error bars represent one standard deviation from the mean.

Deconjugation of TDCA and GDCA by Free *Lactobacillus reuteri* Strains (FIGS. 5 and 6)

Results

FIGS. 5 and 6 show the deconjugation of taurodeoxycholic acid and glycodeoxycholic acid as measured by HPLC in in-vitro assay using 0.2 grams of free *Lactobacillus reuteri* (NCIMB 701359, NCIMB 701089, NCIMB 702656, NCIMB 11951, ATCC 23272 and LMG 9213) over time. NCIMB 701359, NCIMB 701089 and ATCC 23272 strains have the greatest degree of bsh activity as measured by HPLC, again limited by the resolution of the study.

Materials and Methods

Bacteria and Culture Conditions

The bacterial strains used in this study are *L. reuteri* NCIMB 701359, *L. reuteri* NCIMB 701089, *L. reuteri* NCIMB 702656, *L. reuteri* NCIMB 11951, *L. reuteri* ATCC 23272, and *L. reuteri* LMG 9213. The bacteria were inoculated from single colony and passaged for twice with 1% inoculums. The bacteria were cultivated in sterile de Man, Rogosa, Sharpe (MRS, Difco) broth at 37° C. for 20 hours every time. Grown cultures were isolated by centrifugation and collected bacteria cells were used in the following BSH assay.

Measurement of BSH Activity

To measure the BSH activity, 0.2 g of collected bacteria were added into 100% MRS supplemented with a combination of sodium glycocholate and sodium taurocholate at 5 mM (0.2 g of bacteria/20 ml MRS supplemented with 5 mM GDCA and 5 mM TDCA). Bacteria were then incubated anaerobically at 37° C., and supernatant was sampled after 1, 3, 5, and 7 hours to determine the conjugated bile salt concentrations in the reaction tubes. Briefly, 500 μl samples were acidified with 5 μl of 6N HCl after removing bacteria cells by centrifugation at 10000 g for 3 min. The supernatants were then supplemented with 500 μl of Methanol containing 4 mM GCA (glycocholic acid) as internal standard. The samples were vortexed for 10 min and centrifuged at 1000 g for 15 min. The samples were filtered through 0.45 μM filter before being analyzed by HPLC. HPLC analysis of bile salts followed the procedure described by Jones et. al.

Highly bsh Active *L. reuteri* and Reduction of Cholesterol

Materials and Methods

The bsh activity of Lactobacilli strains was calculated by the standard HPLC assay for TDCA and GDCA described in materials and methods sections above. Rates of xDCA removal were calculated by taking the concentration of GDCA or TDCA removed from simulated intestinal contents at the endpoint and subtracting the baseline value. The amount of DCA produced, or xDCA removed, was divided by the mass of microcapsules used and multiplied by the volume of simulated intestinal contents used and divided by the time elapsed, in hours, from baseline to endpoint. This was done by the equation: xDCA reduced=μmol DCA produced or xDCA reduced/g microcapsule/h.

Results

Table 2 shows the bsh activity of *Lactobacillus reuteri* strains tested preclinically or clinically and expressed as a rate (μmol DCA/g/hr) measured over 5 hours and over 30 minutes. Although, *Lactobacillus reuteri* (LabMet) was shown to lower cholesterol preclinically, high doses of *L. reuteri* and high frequency dosing was required. The more bsh active *Lactobacillus* reuteri (NCIMB 701359) which lowered cholesterol in preclinical studies was confirmed to reduce cholesterol significantly in human clinical trials. The higher rate of bsh activity was presumed to be responsible for the activity and there is considerable evidence supporting the claim that a threshold level of bsh activity is required for free cells delivered at high daily doses. It appears that organisms that degrade >50 μmol GDCA/gram/hour and >2 μmol TDCA/gram/hour measured over 1 hour and 5 hours, respectively and that are delivered in the quantity of $10^6$-$10^{12}$ organisms are sufficient for cholesterol lowering. For this reason, the even more bsh active *Lactobacillus reuteri* (NCIMB 701089) are predicted to reduce cholesterol and perform well in preclinical and clinical studies. In addition, bsh activity was measured with the same HPLC assay for TDCA and GDCA; however, the average rate was calculated over a 30 minute period. This provides an accurate determination of the true enzymatic rate, as the xDCA deconjugation curve is more linear between 0 and 30 minutes and the reaction is not limited by the low availability of substrate seen at later time points.

Materials and Methods are the same as for the HPLC assay section described above.

Efficacy and Safety of Highly bsh Active Microencapsulated *Lactobacillus reuteri* (NCIMB 701359) in Syrian Golden F1B Hamsters (Table 3)

Results

Table 3 shows the lipid endpoint percent change from control values for F1B hamsters induced to be hypercholesterolemic and then treated by gavages with either microencapsulated or free *Lactobacillus reuteri* (NCIMB 701359). While there are similar reductions of total cholesterol between groups, there is increased LDL-C reduction, less HDL-C reduction, and improved triglyceride removal with the free organism in this model. This results in a dramatic difference in overall atherogenic index (AI) and shows that while there are advantages to microencapsulation in terms of improved delivery and survival, there are also advantages to delivering highly bsh active free organism in that an improved lipid profile may be obtained.

Materials and Methods

A total of 38, 7-8 week old Bio F1B Syrian golden hamsters were purchased from Biobreeders, USA. Upon delivery the animals were given a week of acclimatization. Animals were housed one per cage in a temperature and humidity controlled room with a twelve hour inverted light-dark cycle with food and water available ad libidum. After acclimatization the animals were weighed and blood was collected to assess baseline lipids as described below.

Hypercholesterolemia was induced by five weeks of feeding with Test diet containing 0.05% cholesterol. Food consumption and weight gain was monitored weekly. Blood was collected after four and five weeks of induction and analyzed for lipid levels. Additionally, safety markers were assessed prior to initiation of treatment (five weeks of induction). Fecal samples were collected on the final day of the induction period and assessed for bile acid content.

Any animals that did not show hypercholesterolemia after five weeks of feeding with the hypercholesterolemia inducing diet were excluded (5 animals). The remaining animals were then assigned to one of three treatment groups by block randomization based on serum LDL levels and adjusted to equalize the average weight of each group (n=11 for each group). After randomization, animals were administered treatment by gavage for six weeks.

During the treatment period feeding with the hypercholesterolemic test diet continued. Food intake and weight was monitored on a weekly basis and blood lipid levels were measured on a biweekly basis. After six weeks of treatment endpoint fecal samples were collected and the animals were sacrificed by carbon dioxide. Blood was collected by cardiac puncture for analysis of endpoint lipids, safety markers and hematology. During necropsy, livers from representative animals of each group were collected for histological analysis.

Efficacy and Safety of less bsh Active Microencapsulated *Lactobacillus reuteri* (LabMet) Containing Yogurt in Lowering Lipids (Table 4)

Results

Table 4 shows the percent change in fasting lipids of mildly hypercholesterolemic subjects in response to consumption of microencapsulated *Lactobacillus reuteri* (LabMet) over a 6-week treatment period. The result shows some change in serum cholesterol over control with reduced levels of serum triglycerides.

Materials and Methods

This study examined the efficacy of the less bsh active microencapsulated *Lactobacillus reuteri* (LabMet) containing probiotic yogurt compositions on health parameters related to degenerative disease in humans.

It was anticipated that consumption of the probiotic product would induce favourable shifts in risk markers for several debilitating diseases of increasing age and that probiotic consumption would favourably alter lipids versus conventional treatments in hyperlipidemic individuals.

The study design was a multi phase/washout, randomized, double blinded, controlled trial in which subjects received control yogurts or test yogurts over a 6 week period followed by a 6 week washout prior to following phases.

A total of 30 healthy males and females, aged 18-60 yr, were randomized with plasma LDL-C 130-260 mg/dl, TG levels below 400 mg/dl, and a body mass index (BMI) of 22-32 kg/m$^2$.

Metabolic diets of precisely known composition were provided to subjects under strict supervision at a clinical research facility. Diets were nutritionally adequate and provided 100% of energy requirements. In addition, the subjects received one test yogurt per day for the treatment period.

Twelve-hour fasting blood samples were collected at the beginning and end of each of the phases of the trial. Blood samples obtained on day 1 and 2 were used to measure baseline values for different study measurements, whereas blood samples obtained on the last days were used to measure final values for serum lipid levels.

Efficacy and Safety of Highly bsh Active Microencapsulated *Lactobacillus reuteri* (NCIMB 701359) Containing Yogurt in Lowering Lipids (Tables 5 and 6)

Results

Tables 5 and 6 show the percent change in fasting lipids in hypercholesterolemic subjects in response to consumption of the more highly bsh active *Lactobacillus reuteri* (NCIMB 701359) over a 6-week treatment period. The result shows significant decreases in total and LDL cholesterol as well as in ApoB as would be predicted from the bsh activity values (26.4 μmol GDCA/gram/hour and 182.6 μmol TDCA/gram/hour). This randomized, double blinded, parallel arm study was well powered and well controlled; thus, any cholesterol lowering was due to the probiotic ingredient.

Materials and Methods

This study examined the efficacy of the highly bsh active microencapsulated *Lactobacillus reuteri* (NCIMB 701359) containing probiotic yogurt formulations on health parameters related to degenerative disease in humans.

The objective was to evaluate the effects of consumption of a yogurt formulation containing alginate poly-L-lysine alginate (APA) microencapsulated highly bile salt hydrolase (bsh)-active *Lactobacillus reuteri* (NCIMB 701359) on plasma lipids levels in hypercholesterolemic adults and access the relative changes of plasma LDL-cholesterol concentration in hypercholesterolemic adults after 6 weeks of product consumption versus control product.

The experiment involved a multi-centric (5 centers) double-blinded randomized parallel-arm placebo controlled trial. Subjects were instructed to follow Health Canada dietary recommendations, which are intended to help reduce risks of obesity and heart disease. The study duration was 10 weeks including 2-week wash-out, 2-week run-in periods and a 6-week treatment period. During the wash-out period, subjects followed dietary instructions only. During the run-in period, placebo was taken. The treatment or placebo product was taken during the whole treatment period.

A total of 120 healthy males and females between the ages 18-74, with LDL-Cholesterol >3.4 mmol/L, and TG levels <4.0 mmol/L, and a BMI range 22-32 kg/m² were randomized and 109 subjects were evaluated as-per-protocol.

Twelve-hour fasting blood samples were collected at the beginning and end of the treatment period. Blood samples obtained on day 1 and 2 were used to measure baseline values for different study measurements, whereas blood samples obtained on the last days were used to measure final values for serum lipid levels.

Identifying Highly bsh Active Bacteria (FIG. 7 and Table 7)
Results

The MRS-TDCA-plate precipitation zone screening assay show that, as a method for determining bsh activity TDCA, plating is crude and may not be sufficient for identifying highly bsh active candidate cholesterol lowering probiotics. As can be seen, the more bsh active cultures have larger zones of precipitation; however, in cases in which the DCA precipitate is more densely concentrated, screening with TDCA plates alone does not identify the most highly bsh active organisms as potential candidates. For this reason an assay with more resolution, such as an HPLC assay, which quantifies the bsh activity for glyco- and tauro-conjugates may be required.

Figure 7:
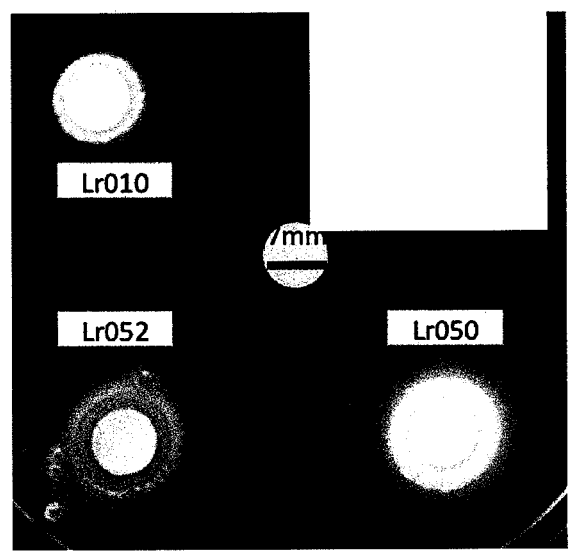
FIG. 7 shows the size of precipitation zone of 3 bsh active *Lactobacillus reuteri*: Lr010: *Lactobacillus reuteri* (LabMet), Lr052: *Lactobacillus reuteri* (NCIMB 701089), and Lr050: *Lactobacillus reuteri* (NCIMB 701359).

FIG. 7 shows three bsh active *Lactobacillus reuteri* grown anaerobically on an MRS-TDCA plate for 24 hours. The size of precipitation zone and density of precipitation are clearly different for each organism.

Table 7 shows the diameter of precipitation (mm) of deoxycholic acid (DCA) as measured on MRS-TDCA plates after 24 hours of anaerobic growth by filter discs impregnated with culture. The values are averages of triplicate measurements on 3 MRS-TDCA agar plates. Comparison of the results from Table 7 with those from Table 2 shows that the zone of precipitation assay does not always differentiate highly bsh active bacteria as it is clear that LR050 has a larger precipitation zone than LR052 but HPLC shows that in fact LR052 is more highly bsh active.

Materials and Methods

*Lactobacillus* cultures were grown overnight in MRS media at 37° C. 500 µl of each culture was centrifuged in a pre-weighed Eppendorf. The supernatant was removed and the pellets were weighed. The pellets were resuspended with MRS to get same 1:10 w/v ratio and 10 µl of each culture was added to filter disks in duplicate on different MRS-TDCA agar plates. The plates were incubated anaerobically at 37° C. and measurements were made.

Figure 8:
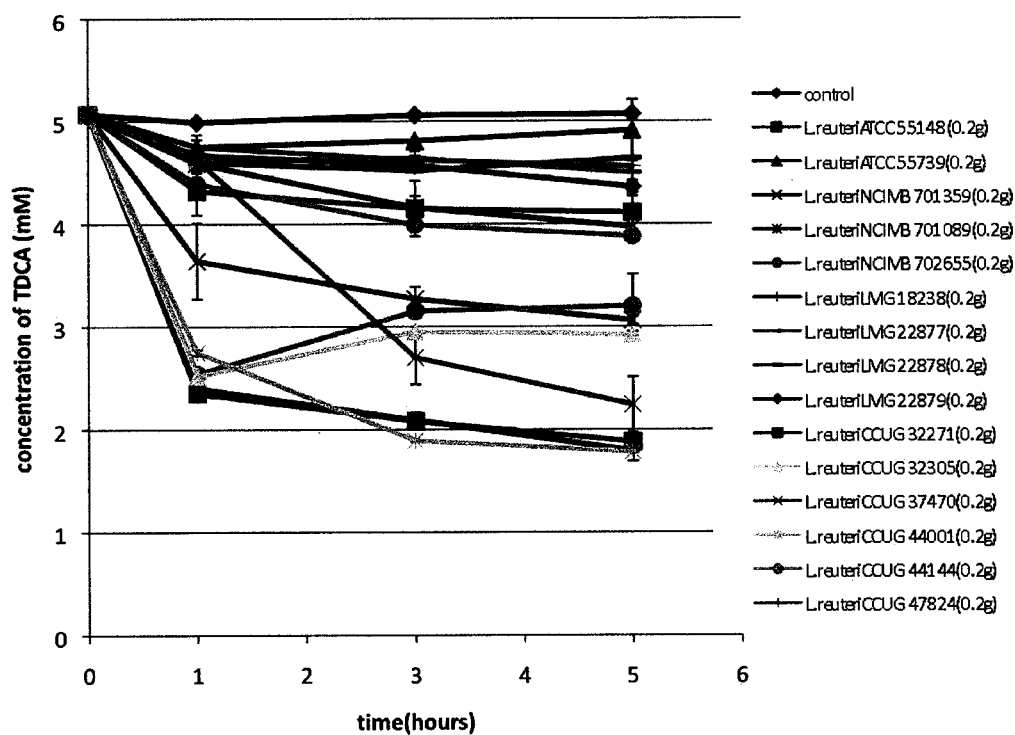
FIG. 8 shows deconjugation of TDCA by free *Lactobacillus reuteri* strains (ATCC 55148, ATCC 55739, NCIMB 701359, NCIMB 701089, NCIMB 702655, LMG 18238, LMG 22877, LMG 22878, LMG 22879, CCUG 32305, CCUG 37470, CCUG 44001, CCUG 44144, CCUG 47824) over time. The experiment was performed in triplicate and error bars represent one standard deviation from the mean.
Figure 9:
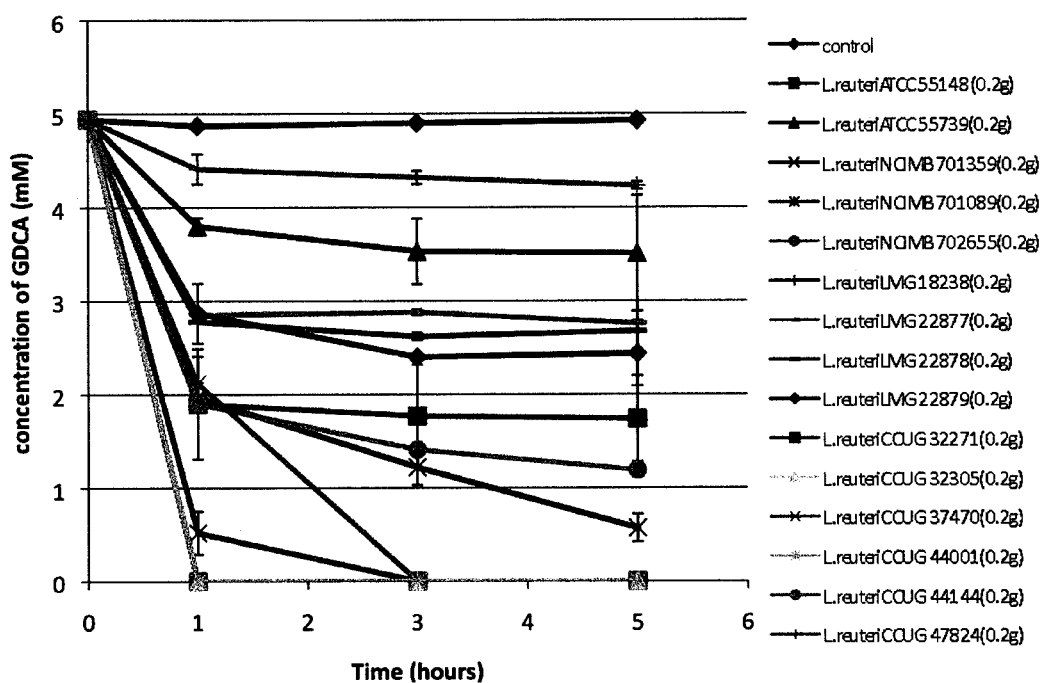
FIG. 9 shows deconjugation of GDCA by free *Lactobacillus reuteri* strains (ATCC 55148, ATCC 55739, NCIMB 701359, NCIMB 701089, NCIMB 702655, LMG 18238, LMG 22877, LMG 22878, LMG 22879, CCUG 32305, CCUG 37470, CCUG 44001, CCUG 44144, CCUG 47824) over time. The experiment was performed in triplicate and error bars represent one standard deviation from the mean.

Deconjugation of TDCA and GDCA by Free *Lactobacillus reuteri* Strains (FIGS. 8 and 9)
Results FIGS. 8 and 9 show the deconjugation of taurodeoxycholic acid and glycodeoxycholic acid, as measured by HPLC, in an in-vitro assay using 0.2 grams of free *Lactobacillus reuteri* (ATCC 55148, ATCC 55739, NCIMB 701359, NCIMB 701089, NCIMB 702655, LMG 18238, LMG 22877, LMG 22878, LMG 22879, CCUG 32271, CCUG 32305, CCUG 37470, CCUG 44001, CCUG 44144, CCUG 47824) over time. The results show that strains ATCC 55148, NCIMB 701359, NCIMB 701089, NCIMB 702655, LMG 18238, CCUG 32271, CCUG 32305, CCUG 37470, CCUG 44001 and CCUG 44144 have particularly high bsh activity as measured by HPLC.

Materials and Methods
Bacteria and Culture Conditions

The *Lactobacillus reuteri* strains were cultivated in sterile de Man, Rogosa, Sharpe (MRS) broth at 37° C. for 20 hours. Grown cultures were isolated by centrifugation and collected bacteria cells were used in the following BSH assay.

Measurement of BSH Activity

To measure the BSH activity, collected bacteria were added into 100% MRS supplemented with a combination of sodium glycodeoxycholate and sodium taurodeoxycholate both at 5 mM (0.2 g bacteria cells/20 ml MRS supplemented with GDCA and TDCA). Bacteria were then incubated in the reaction broth anaerobically at 37° C. with minimal shaking (100 rpm), and supernatant was sampled at intervals of 2.5 hours and processed to determine the conjugated bile salt concentrations. Briefly, 500 µl samples were acidified with 5 ul of 6N HCl after removing bacteria cells by centrifugation at 10000 g for 3 min. The supernatants were then supplemented with 500 µl of Methanol containing 4 mM GCA (glycocholic acid) as internal standard. The samples were vortexed for 10 min and centrifuged at 1000 g for 15 min. The samples were filtered through 0.22 µM filter before being analyzed by HPLC. HPLC analysis of bile salts followed the procedure described by Jones et al. 2003.

Bile Salt HPLC Analysis

HPLC analysis of bile salts followed the procedure described by Jones et al. 2003. The analysis was performed on a reverse-phase C-18 column: LiChrosorb RP-18, 5 µm, 250×4.6 mm. The HPLC system comprised of two ProStar 210 solvent delivery modules, a ProStar 320 UV-VIS detector, a ProStar 410 autosampler and Galaxie Chromatography Data system (version 1.9.3.2). A mixture of methanol and 50 mM sodium acetate buffer adjusted to pH4.3 with o-phosphoric acid (70:30, v/v) was applied as mobile phase with a flow rate of 1.0 ml/min. The detector was set at 210 nm and all the measurements were performed at room temperature.

Example 2—High BSH Activity

General Materials and Methods

Bacterial seeding and growth: the surfaces of frozen glycerol bacterial stocks were scratched with a sterile wooden stick to streak MRS agar plates. After an overnight incubation at 37° C. under anaerobic conditions, a single colony of *L. reuteri* NCIMB 701359 was picked with a metallic loop under sterile conditions and transferred into a tube containing 10 mL of MRS. The cultures were incubated overnight at 37° C. for experimental use.

Microencapsulation of *L. reuteri* NCIMB 701359: microcapsules were prepared with an 8% cell load and a 1.75% alginate concentration using a 200 µm sized nozzle. The coating process was the following: first, alginate beads were drained of $CaCl_2$; second, alginate beads were washed in 0.85% (w/v) NaCl for 10 minutes; third, alginate beads were coated in 0.1% (w/v) ε-PLL for 20 minutes; fourth, alginate-PLL microcapsules were washed with 0.85% (w/v) NaCl for 10 minutes; fifth, alginate-PLL microcapsules were coated with 0.1% (w/v) alginate for 20 minutes; and finally the alginate-PLL-alginate microcapsules were washed with 0.85% (w/v) NaCl for 10 minutes.

BSH assay for frozen and lyophilized free cells: frozen free cells were thawed, centrifuged, and washed and were added (0.05 g) to 20 ml of MRS containing 5 mM TDCA and 5 mM GDCA. Lyophilized free cells were added (0.15 g) to 20 ml of MRS containing 5 mM TDCA and 5 mM GDCA. Samples were taken out after 30 min and were analyzed with HPLC. Controls were the medium alone and freshly prepared microcapsules grown in MRS.

BSH assay for microcapsules: thawed and washed microcapsules (sample between 0.3 g and 2.5 g, depending on relative activity) were added to 20 ml of MRS containing 5 mM TDCA and 5 mM GDCA. Samples were taken out after 30 min and were analyzed with HPLC. Controls were the medium alone and freshly prepared microcapsules grown in MRS. 0.3 g of microcapsules contained 0.03 g pellet of free cells.

HPLC assay for BSH activity: analyses were performed on a reverse-phase C-18 column (LiChrosorb RP-18 250 nm×4.6 mm, 5 µm) at a flow rate of 1.0 ml/min. The mobile phase was a mixture of methanol and 50 mM sodium acetate buffer (pH 4.3 adjusted with o-phosphoric acid) in 70:30 ratio and detection was measured at 210 nm. The bsh activity was evaluated by the amount of deconjugated GDCA and TDCA in samples per hour per gram microcapsules.

A. Improved bsh Activity Through Fermentation (Tables 8-10)

Materials and Methods

Increase of bsh activity based on carbon and nitrogen sources: *Lactobacillus reuteri* NCIMB 701359 cells were grown by the general method described above. 1% of *L. reuteri* NCIMB 701359 was inoculated into modified MRS medium with different sources of carbon and nitrogen. Inoculated cultures were incubated at 37° C. for 24 h. Following incubation time, 0.05 g or 0.1 g of cell pellet was added to 20 ml of MRS containing 5 mM TDCA and 5 mM GDCA. Samples were removed after 0.5 h and 1.5 h, and were analyzed with HPLC. MRS was used as the control growth media. Analyses were performed by HPLC as described in the general methods above.

Increase of BSH activity based on pH and harvest time: *Lactobacillus reuteri* NCIMB 701359 cells were grown by the general method described above. 1% of *L. reuteri* NCIMB 701359 was inoculated into growth medium with carbon and nitrogen sources and pH adjusted to pH 5, 6 and 6.8 by adding NaOH or HCl. Inoculated cultures at different pH conditions were incubated at 37° C. for harvest times of 12 h to 48 h. Following incubation time, 0.05 g or 0.1 g of cell pellet was added to 20 ml of MRS containing 5 mM TDCA and 5 mM GDCA. Samples were removed after 0.5 h and 1.5 h, and were analyzed with HPLC as described in the general methods above. Controls were grown in non-modified MRS medium.

Results

The most favourable results from a carbon source for *Lactobacillus reuteri* NCIMB 701359 fermented in modified MRS, increasing bsh activity and yield, was maltose. GDCA and TDCA were deconjugated at rates of 2,253 (µmol/g/h) and 173 (µmol/g/h) respectively and a yield of 0.015 g/ml was maintained (Table 8). The most favourable results from nitrogen sources for *Lactobacillus reuteri* NCIMB 701359 fermented with this carbon source (maltose) and looking for increased GDCA (µmol/g/h) deconjugation, TDCA (µmol/g/h) deconjugation (HPLC), and yield (g/ml) was a combination of peptone No. 3, yeast extract, malt extract, and cysteine. GDCA and TDCA were deconjugated at rates of 21,185 (µmol/g/h) and 2,323 (µmol/g/h) respectively and a yield of 0.013 g/ml was maintained (Table 9). The most favourable results for harvest time and initial pH for *Lactobacillus reuteri* NCIMB 701359 fermented in either the above-noted media (maltose+peptone No. 3+yeast extract+malt extract+cysteine) or MRS, looking for increases for GDCA (µmol/g/h) deconjugation, TDCA (µmol/g/h) deconjugation (HPLC), and yield (g/ml) was a pH of 5 at a harvest time of 12-20 hours (Table 10).

These results show that conditions including carbon and nitrogen sources, pH, and harvest time achieve high bsh activity and cell yield with *Lactobacillus reuteri* NCIMB 701359; these conditions produce a highly active product, which maintains high bsh levels over a shelf life in supplement or functional food format, and is cost effective to produce commercially. This data shows that probiotic cells with bsh producing machinery are readily fermented with defined media and conditions to achieve therapeutic levels of enzymatic activity and commercially viable levels of biomass. This process is useful to make bsh active probiotics commercially viable for lipid lowering and other applications.

Figure 10:
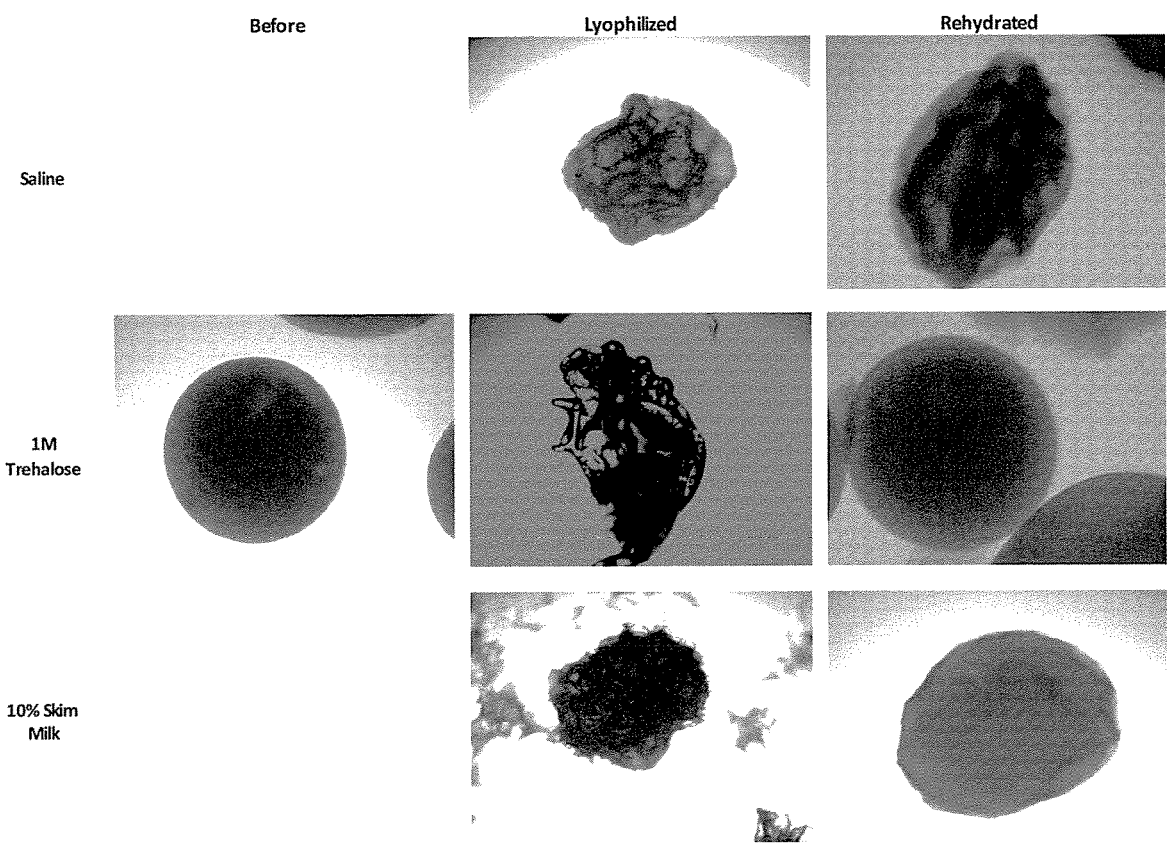
FIG. 10 shows a representative set of microcapsule morphology photomicrographs using different lyoprotectant conditions at 7:3 microcapsule to lyoprotectant for saline, 1M trehalose, and 10% skim milk used for lyophilisation and rehydration of microencapsulated *Lactobacillus*.

B. Improved bsh Activity by Lyophilization (Table 11 and FIG. 10)

Materials and Methods

Lyophilization storage conditions for high BSH activity: Microcapsules containing *Lactobacillus reuteri* NCIMB 701359 were prepared by the general method described above. Microcapsules were stored in a 7:3 ratio of microcapsules to lyoprotectant solution as follows: 1M trehalose, 10% maltodextrin, 1% inulin, 10% maltodextrin and 0.33% yeast extract, 1M trehalose and 0.33% yeast extract, 1% inulin and 0.33% yeast extract, 10% maltodextrin and 1% casein hydrolysate, and 10% skim milk. Slurries containing microcapsules and lyoprotectant solution were lyophilized and stored at 4° C. for 0, 1, 2, 3, 4, 5 and 6 weeks in individual aliquots. At each timepoint, duplicate samples of lyophilized microcapsules containing each lyoprotectant were rehydrated with saline. The bsh assay for microcapsules described above was used to prepare samples for HPLC analysis by the general method above.

Free *Lactobacillus reuteri* NCIMB 701359 was prepared by the general method described above. Lyoprotectants were added to the free cell slurry at a final concentration of: 10% maltodextrin and 0.33% yeast extract. Slurries were lyophilized and stored at 4° C. or RT for 0, 1, 2, and 3 months in individual aliquots. At each time point, duplicate samples of lyophilized cells containing each lyoprotectant were rehydrated with saline. The bsh assay for lyophilized material described above was used to prepare samples for HPLC analysis by the general method above.

Results

The most favourable results from a lyoprotectant for *Lactobacillus reuteri* NCIMB 701359, increasing bsh activity were 10% maltodextrin and 0.33% yeast extract, 1% inulin and 0.33% yeast extract, and 1% inulin (Table 11).

These results show that lyoprotectants maintain high bsh activity for *Lactobacillus reuteri* NCIMB 701359; the lyoprotectant maintains microcapsule morphology upon rehydration (FIG. 10), maintains high bsh levels over a shelf life in supplement or functional food format, and is cost effective to produce commercially. This data shows that free or microencapsulated probiotic cells with bsh producing machinery are readily lyophilized with lyoprotectants to maintain therapeutic levels of enzymatic activity. This process is useful to make lyophilized bsh active probiotics commercially viable for lipid lowering and other applications.

C. Improved bsh Activity by Liquid Storage (Table 12)

Materials and Methods

Liquid storage conditions for BSH activity: Microcapsules containing *Lactobacillus reuteri* NCIMB 701359 were prepared by the general method described above. Microcapsules were stored in a 1:1 ratio of microcapsules to preservative solutions as follows: 5% growth media, 10% growth media, 20% growth media, 10% MRS media, yogurt, culture supernatant, 1% maltose, 0.85% saline, 1% malt extract, 1% inulin, 10% sorbitol, 0.33% yeast extract, 1% inulin and 0.33% yeast extract and 1M fructose. The resulting microcapsules were stored in preservative solutions at 4 degrees for short-term storage of 4 days in individual aliquots. Duplicate samples of microcapsules containing each liquid preservative solution were removed from storage medium and washed with saline. The bsh assay for microcapsules described above was used to prepare samples for HPLC analysis by the general method above.

Results

The most favourable results from a liquid storage condition for *Lactobacillus reuteri* NCIMB 701359, considering bsh activity after 4 days liquid storage, were yogurt (1:1), 5% growth media (1:1), 10% growth media, 20% growth media (1:1), culture supernatant (1:1), and 10% MRS (1:1) (Table 12).

These results show liquid storage conditions maintain high bsh activity with *Lactobacillus reuteri* NCIMB 701359; these conditions result in production of a highly active product, which maintains high bsh levels during temporary liquid storage, and which is cost effective to use in the commercial process. This data shows that specific storage conditions are beneficial for storage in liquid media to achieve therapeutic levels of enzymatic activity. This process is useful in maintaining bsh activity during short term storage and makes the production process commercially viable for producing bsh active probiotics for lipid lowering and other metabolic disease therapeutic applications.

D. Improved Bsh Activity Through Flash Freezing (Table 13)

Materials and Methods

Flash freezing storage conditions for bsh activity: Microcapsules containing *Lactobacillus reuteri* NCIMB 701359 were prepared by the general method above. Microcapsules were stored in a 1:1 ratio of microcapsules to cryoprotectant solution as follows: 1M trehalose, 1M fructose, 1% inulin, 1M maltose, 1M lactose, 1M sucrose, 10% PEG 8000, 0.85% saline, 10% skim milk, 10% starch or 10% fructooligosaccharides. Slurries containing microcapsules and cryoprotectant solution were slowly passed through a sterile syringe to form spherical droplets which were suspended in liquid nitrogen. The resulting flash frozen pellets were isolated from liquid nitrogen and stored at −80° C. in individual aliquots. Immediately and after 3 weeks storage, duplicate samples of pelleted microcapsules containing each cryoprotectant solution were removed from storage medium and washed with saline. The bsh assay for microcapsules described above was used to prepare samples for HPLC analysis described in the general methods above.

Free *Lactobacillus reuteri* NCIMB 701359 were prepared by the general method above. Free cell pellet was re-suspended in spent media at a 1:1 ratio of cells to spent media. The resulting cell slurry was slowly passed through a sterile syringe to form spherical droplets which were suspended in liquid nitrogen. The resulting flash frozen pellets were isolated from the liquid nitrogen and stored at −80° C. Duplicate samples of pelleted cells containing spent media cryoprotectant solution were removed from storage medium. The bsh assay for free cells described above was used to prepare samples for HPLC analysis described in the general methods above.

Results

The most favourable results from cryopreservative media for *Lactobacillus reuteri* NCIMB 701359, flash frozen in liquid nitrogen, when considering capsule morphology and/or % remaining bsh activity immediately post flash freezing and at 3 weeks, included 1:1 free or microencapsulated bacteria to cryopreservative solution with maltodextrin and yeast extract, inulin, trehalose, fructose, sucrose, lactose, maltose and spent media at indicated concentrations (Table 13).

These results show that cryopreservation conditions when flash freezing in liquid nitrogen for frozen storage achieve high bsh activity and good microcapsule morphology with encapsulated *Lactobacillus reuteri* NCIMB 701359; allowing production of a product with high bsh levels over an extended shelf life in supplement or functional food format, and which is cost effective for commercial production. This data shows that free or microencapsulated probiotic cells with high bsh activity are readily prepared under several cryopreservative conditions and flash frozen in liquid nitrogen achieves therapeutic levels of enzymatic activity and excellent microcapsule morphology. This process is useful to make bsh active probiotics commercially viable for lipid lowering and other applications.

High BSH Activity: Benefits of Earlier Fermentation Harvest Times (i.e. 6-12 Hours) to Produce Stable Highly BSH Active Probiotics Materials and Methods A 1% inoculum of *L. reuteri* NCIMB 701359 was used in MRS medium, adjusted to pH 5 and with optimized sources of carbon (maltose), nitrogen (peptone No. 3, yeast extract, malt extract) and supplemented cysteine. Inoculated cultures were incubated at 37° C. and samples were taken at 2, 4, 6, 8, 9, 10, 11, 12, 14 and 16 h. At each time point, cultures were analyzed for cell yield and BSH activity. In order to assess BSH activity, 0.005 g of cell pellet was added to 20 ml of MRS containing 5 mM TDCA and 5 mM GDCA. Samples were removed after 0.5 h, and were analyzed by HPLC. Analyses were performed on a reverse-phase C-18 column (LiChrosorb RP-18 250 nm×4.6 mm, 5 μm) at a flow rate of 1.0 ml/min. The mobile phase was a mixture of methanol and 50 mM sodium acetate buffer (pH 4.3 adjusted with o-phosphoric acid) in 70:30 ratio and detection was measured at 210 nm. The BSH activity was evaluated by the amount of deconjugated GDCA produced per ml of culture or per gram of cell pellet per hour.

To assess stability, concentrated samples of *L. reuteri* NCIMB 701359, taken from each time point after the BSH activity plateau was reached (9-16 h), are lyophilized. Shelf-life stability of the resulting powders are measured in real-time (room temperature) and accelerated (37° C., 60% relative humidity conditions.

Results

Using non-optimized media and conditions for *L. reuteri* NCIMB 701359, BSH activity reaches a maximum in the late stationary phase of growth (i.e. after 48 hours). As shown in Table 14, by employing optimized media and growth conditions for *L. reuteri* NCIMB 701359, it was shown that both BSH activity and cell yield reached a plateau during log phase of growth, after 9 hours of incubation time (19,071 U/g cell pellet/h and 0.017 g/mL respectively). Even after only 8 hours of incubation, high BSH activity and cell yield was seen (10,085 U/g cell pellet/h 0.015 g/mL respectively), and although BSH activity was not measurable at 6 hours, gene expression was certainly turned on and high levels of BSH enzyme produced at a time point between 6 and 8 hours. Finally, for some strains of probiotic bacteria, early harvest times can result in cells which are less stressed, with a higher nutrient and lower metabolic waste environment, as compared to cells isolated in late stationary phase. This added vigour can be especially beneficial for some strains when the cells are exposed to potentially stressful cryo-freezing or lyophilisation, as shown by increased stability in final format.

Without wishing to be bound by theory, by harvesting early, for example 6-12 hours, there is a healthier biomass and, in combination with appropriate lyoprotectants, would result in improved stability. By harvesting later, for example, 13-24 hours, the cells build up a stress response and are therefore more responsive and stable when lyophilized. Depending on the strain, process, and other factors, the choice of optimal harvest time can be determined.

The present results demonstrate that an earlier harvest time (i.e. 6-12 hours) is readily exploited to link high BSH activity and optimal cell yield with a final product that is stable and a process that is cost-effective commercially. Probiotic cells with BSH producing machinery are readily fermented with optimized media and conditions to achieve therapeutic levels of enzymatic activity and commercially viable levels of biomass at the late log phase of growth. An added advantage of early harvest optimization is the potential for lesser macronutrient requirements, specifically carbon and nitrogen sources, when fermented at a commercial scale, resulting in a more cost-effective overall process.

Again, the specific harvest time for probiotic isolation is strain dependent and based on a defined media that can meet the desired specifications before entry into stationary phase. This process is readily exploited to make the majority of BSH active probiotics commercially viable for lipid lowering and other applications.

High BSH Activity: Cysteine Supplementation in Growth Media, as a Cryoprotectant or as a lyoprotectant for improving enzymatic activity, Cell Viability and Shelf-Life Stability of BSH Active Probiotics Materials and Methods Cysteine supplementation in growth media: 1% of *L. reuteri* NCIMB 701359 was inoculated into modified MRS medium, adjusted to pH 5 and with optimized sources of carbon (maltose) and nitrogen (peptone No. 3, yeast extract, malt extract) and supplemented with or without cysteine at 0.01%. Inoculated cultures were incubated at 37° C. for 16 hours and were analyzed for BSH activity as previously described.

Cysteine supplementation as a cryoprotectant: *L. reuteri* NCIMB 701359 was fermented, concentrated and flash frozen in liquid nitrogen. Bacterial concentrate was supplemented with 7.5% maltodextrin and 0.05% cysteine or without cryoprotectants (spent media alone).

Bacterial pellet (frozen with no cryoprotectants) was thawed and microencapsulated into alginate-poly-L-lysine-alginate microcapsules (according to general methods). Microcapsules containing *L. reuteri* NCIMB 701359 were then supplemented with a variety of cryoprotectants including maltodextrin, inulin, yeast extract and cysteine simulating a twice overall freezing process for the bacterial strain.

Results

Figure 11:
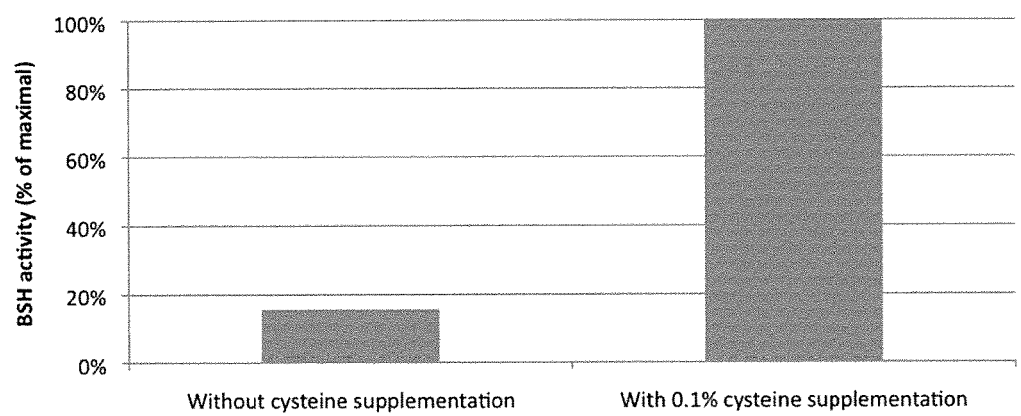
FIG. 11 shows BSH activity of *L. reuteri* NCIMB 701359 after fermentation in optimized media with and without cysteine supplementation (0.01%).

Cysteine supplementation to a defined optimal media, at a concentration of 0.01%, was shown to significantly improve BSH activity of *L. reuteri* NCIMB 701359 by 5-10 times greater than the base defined optimal media (FIG. 11). In addition, cysteine is further beneficial when supplemented as a cryoprotectant or lyoprotectant.

Figure 12:
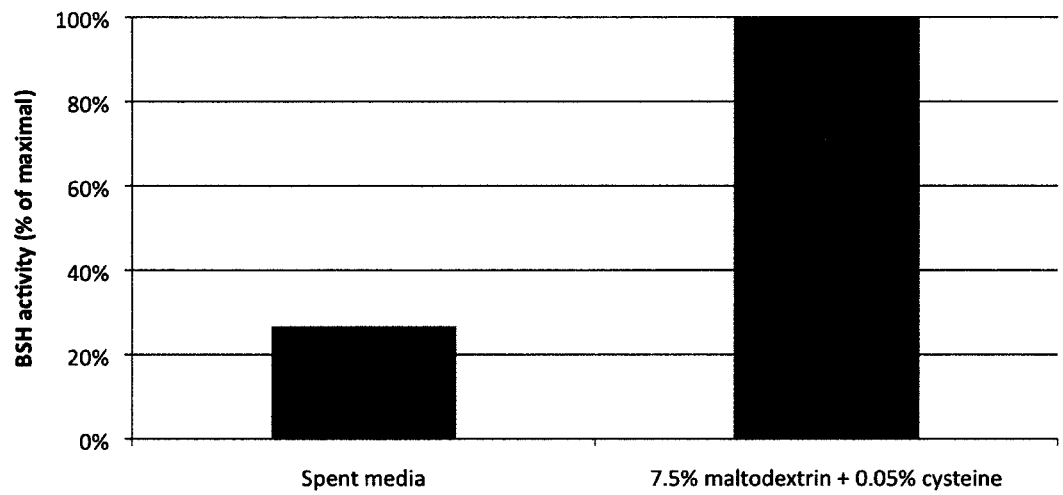
FIG. 12 shows BSH activity of *L. reuteri* NCIMB 701359 after flash freezing in optimized media with and without cryoprotectant supplementation of 7.5% maltodextrin and 0.05% cysteine.
Figure 13:
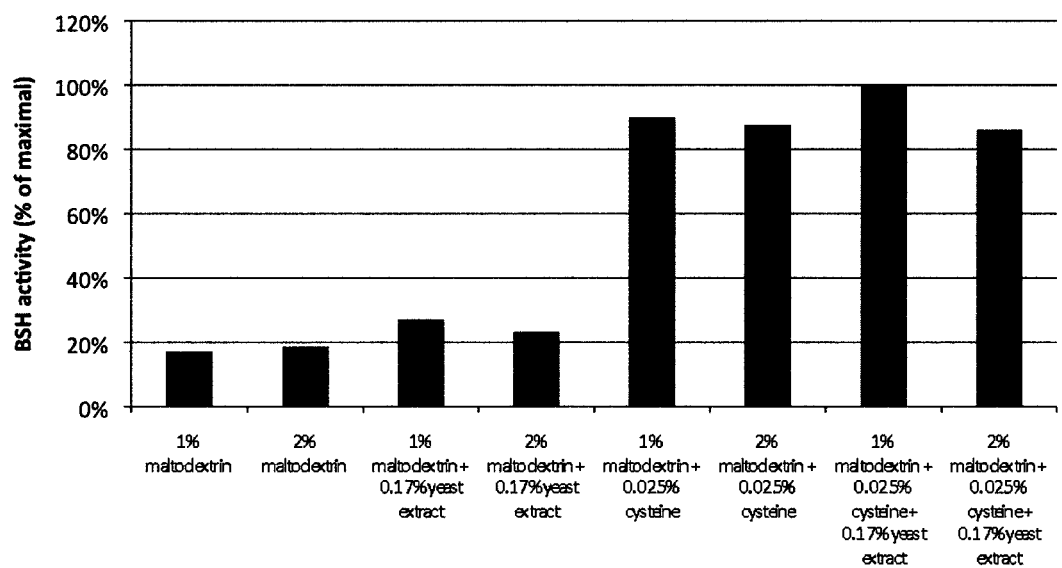
FIG. 13 shows BSH activity of microencapsulated *L. reuteri* NCIMB 701359 (frozen and thawed) after flash freezing in cryoprotectant solutions with and without cysteine supplementation (0.025%).

Cysteine supplementation at 0.05%, in combination with 7.5% maltodextrin, was shown to protect *L. reuteri* NCIMB 701359 from oxidative stress during the cryo-freezing process and increase the BSH activity by 4-fold in comparison to spent media alone (FIG. 12). Furthermore, in protecting microencapsulated *L. reuteri* NCIMB 701359, cysteine was shown to be the key cryoprotectant for the maintenance of BSH activity. Maltodextrin and cysteine was shown to significantly outperform maltodextrin alone or maltodextrin and yeast extract, despite a lower concentration (FIG. 13).

Cysteine supplementation in media or as a protectant is readily used for most probiotics in order to achieve therapeutic targets of BSH activity, notably oxygen sensitive strains, that would not be commercially viable otherwise.

Cysteine is useful as an anti-oxidant and reducing agent, protecting the probiotic from oxidative stress during the cryo-freezing process, such as flash-freezing in liquid nitrogen, or the lyophilisation process. Cysteine can be used to protect thiol-containing proteins from irreversible oxidation during the freezing process. The BSH enzyme can be classified as an N-terminal hydrolase with Cysteine as the N-terminal amino acid. Protection of the free thiol group is useful for catalytic activity.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Two commonly used equations for determining atherogenic index (AI) representing atherogenic risk and used as prognostic indicators patients at risk of developing atherosclerosis Atherogenic Index (AI) = Log(Triglycerides/HDL-Cholesterol)
Atherogenic Index (AI) = (TC-HDL-Cholesterol)/(HDL-Cholesterol)

TABLE 2

BSH activity of free *Lactobacillus reuteri* as measured by HPLC is shown in µmol DCA per gram per hour (µmol DCA/g/hr). Taurodeoxycholic acid = TDCA, Glycodeoxycholic acid = GDCA, Deoxycholic acid = DCA.

|  | TDCA (µmol DCA/g/hr) Average rate (0-5 h) | GDCA (µmol DCA/g/hr) Average rate (0-1 h) | TDCA (µmol DCA/g/hr) Average rate (0-0.5 h) | GDCA (µmol DCA/g/hr) Average rate (0-0.5 h) |
|---|---|---|---|---|
| Free *L. reuteri* (LabMet) | 1.5 | 47.8 | 7.2 | 65.3 |
| Free *L. reuteri* (NCIMB 701359) | 26.4 | 182.6 | 44.0 | 372.0 |
| Free *L. reuteri* (NCIMB 701089) | 77.5 | 424.0 | 93.0 | 805.0 |

TABLE 3

Lipid endpoint values (% change from control) are shown for F1B hamsters induced to be hypercholesterolemic (0.5% dietary cholesterol) (5 weeks) and then treated (6 weeks) by gavages with either microencapsulated or free *Lactobacillus reuteri* (NCIMB 701359) (n = 33).

|  | LDL-C (%) | Total Cholesterol (%) | HDL-C (%) | TG (%) | AI (%) |
|---|---|---|---|---|---|
| Microencapsulated *L. reuteri* (NCIMB 701359) | −23.60 | −16.83 | −11.11 | −5.05 | −11.27 |
| Free *L. reuteri* (NCIMB 701359) | −27.43 | −16.94 | −6.26 | −11.63 | −18.53 |

TABLE 4

Percent change in fasting lipid levels (over control) in mildly hypercholesterolemic human subjects in response to consumption of the less bsh active APA microencapsulated *Lactobacillus reuteri* (LabMet) over a 6 week treatment period (n = 30, as-per-protocol).

|  | LDL-C (%) | Total Cholesterol (%) | HDL-C (%) | TG (%) |
|---|---|---|---|---|
| Microencapsulated *L. reuteri* (LabMet) | −0.07 | −3.63 | −2.37 | −12.51 |

TABLE 5

Fasting lipid levels are given, as percent difference from palcebo, in mildly hypercholesterolemic human subjects in response to consumption of highly bsh active microencapsulated *Lactobacillus reuteri* (NCIMB 701359) over a 6 week treatment period (n = 109, as-per-protocol). Microencapsulated *L. reuteri* (NCIMB 701359)

| Lipid Parameter | % Change (3 wks) | P-Value | % Change (6 wks) | P-Value |
|---|---|---|---|---|
| TC | −2.89 | 0.2321 | −4.86 | 0.0501 |
| LDL-C | −3.83 | 0.1660 | −9.23 | 0.0061 |
| HDL-C | +0.14 | 0.9697 | +0.49 | 0.9101 |
| TG | −23.69 | 0.0275 | +21.05 | 0.0869 |
| ApoB-100 | −3.84 | 0.2056 | −6.66 | 0.0405 |

TABLE 6

Fasting lipid levels are given, as a percent change from placebo, in hypercholesterolemic human subjects, at high risk and very high risk, in response to consumption of the highly bsh active APA microencapsulated *Lactobacillus reuteri* (NCIMB 701359) over a 6 week treatment period (n = 65). Microencapsulated *L. reuteri* (NCIMB 701359)

| Lipid Parameter | % Change (6 wks) | P-Value |
|---|---|---|
| TC | −5.53 | 0.101 |
| LDL-C | −10.22 | 0.024 |
| HDL-C | −0.19 | 0.97 |
| TG | +11.09 | 0.54 |
| ApoB-100 | −10.69 | 0.0082 |

TABLE 7

Diameter of precipitation (mm) of deoxycholic acid (DCA) as measured on MRS-TDCA plates after 24 hours of anaerobic growth by filter discs impregnated with culture. The values are averages of triplicate measurements on 3 MRS-TDCA agar plates.

|  | Lr010 | Lr050 | Lr052 |
|---|---|---|---|
| 2 days | 12.6 | 17.3 | 17 |
| 3 days | 13 | 20 | 18 |
| 4 days | 13.2 | 20.3 | 18.2 |

TABLE 8

Experimental results for determining the carbon source for increasing GDCA (µmol/g/h) deconjugation, TDCA (µmol/g/h) deconjugation (HPLC), and yield (g/ml) for *Lactobacillus reuteri* NCIMB 701359 fermented in modified MRS (yeast extract + beef extract + peptone No. 3) while varying the carbon source.

|  | Yeast extract + Beef extract + Peptone No. 3 | | |
|---|---|---|---|
|  | GDCA (µmol/g/h) | TDCA (µmol/g/h) | Yield (g/ml) |
| Sucrose | 950 | 117 | 0.012 |
| Xylose | 225 | 75 | 0.008 |
| Inulin + Glucose | 2050 | 825 | 0.008 |
| Lactose | 145 | 18 | 0.011 |
| Dextrin | 1640 | 180 | 0.01 |
| Sorbitol + Glucose | 1889 | 689 | 0.009 |
| Glucose (MRS) | 957 | 57 | 0.014 |
| Maltose | 2253 | 173 | 0.015 |

TABLE 9

Experimental results for determining the nitrogen sources increasing for GDCA (µmol/g/h) deconjugation, TDCA (µmol/g/h) deconjugation (HPLC), and yield (g/ml) for *Lactobacillus reuteri* NCIMB 701359 fermented in the carbon source (maltose) while varying sources of nitrogen.

| Malltose | Yeast extract + Beef extract | | | Casein acid hydrolysate + Malt extract | | | Yeast extract + Malt extract | | |
|---|---|---|---|---|---|---|---|---|---|
| (Carbon source) + | GDCA (µmol/g/h) | TDCA (µmol/g/h) | Yield (g/ml) | GDCA (µmol/g/h) | TDCA (µmol/g/h) | Yield (g/ml) | GDCA (µmol/g/h) | TDCA (µmol/g/h) | Yield (g/ml) |
| Peptone No. 3 | 2253 | 173 | 0.015 | 2156 | 167 | 0.018 | 3322 | 933 | 0.018 |
| Tryptone |  |  |  | 843 | 514 | 0.014 | 1013 | 67 | 0.015 |
| Fish peptone |  |  |  | 680 | 80 | 0.005 | 1067 | 107 | 0.015 |
| Soy peptone |  |  |  | 367 | 67 | 0.012 | 689 | 78 | 0.018 |
| Peptone No. 3 + Cysteine |  |  |  |  |  |  | 21185 | 2323 | 0.013 |

TABLE 9-continued

Experimental results for determining the nitrogen sources increasing for GDCA (µmol/g/h) deconjugation, TDCA (µmol/g/h) deconjugation (HPLC), and yield (g/ml) for *Lactobacillus reuteri* NCIMB 701359 fermented in the carbon source (maltose) while varying sources of nitrogen.

| Malltose (Carbon source) + | Yeast extract + Beef extract | | | Casein acid hydrolysate + Malt extract | | | Yeast extract + Malt extract | | |
|---|---|---|---|---|---|---|---|---|---|
| | GDCA (µmol/g/h) | TDCA (µmol/g/h) | Yield (g/ml) | GDCA (µmol/g/h) | TDCA (µmol/g/h) | Yield (g/ml) | GDCA (µmol/g/h) | TDCA (µmol/g/h) | Yield (g/ml) |
| Tryptone + Cysteine | 6271 | 1271 | 0.014 | | | | | | |
| Proteose peptone + Cysteine | | | | | | | 2786 | 671 | 0.014 |
| Casein peptone + Cysteine | 6271 | 1414 | 0.014 | | | | | | |
| Fish peptone + Cysteine | 8415 | 1446 | 0.013 | | | | | | |
| Soy peptone + Cysteine | 1779 | 179 | 0.019 | | | | | | |

TABLE 10

Experimental results for determining the harvest time and initial pH increasing for GDCA (µmol/g/h) deconjugation, TDCA (µmol/g/h) deconjugation (HPLC), and yield (g/ml) for *Lactobacillus reuteri* NCIMB 701359 fermented with either growth media (maltose + peptone No. 3 + yeast extract + malt extract + cysteine) or MRS media at various initial pH values and harvest times.

| | Growth media pH 5 | | | Growth media pH 6 | | | Growth media pH 6.8 | | | MRS media pH 6.8 | | |
|---|---|---|---|---|---|---|---|---|---|---|---|---|
| | GDCA (µmol/g/h) | TDCA (µmol/g/h) | OD (600 nm) | GDCA (µmol/g/h) | TDCA (µmol/g/h) | OD (600 nm) | GDCA (µmol/g/h) | TDCA (µmol/g/h) | OD (600 nm) | GDCA (µmol/g/h) | TDCA (µmol/g/h) | OD (600 nm) |
| 12 h | 19350 | 3475 | 3.12 | 15775 | 3063 | 3.09 | 18752 | 2288 | 2.69 | 201 | 0 | 1.20 |
| 16 h | 19078 | 3772 | 3.18 | 16163 | 3547 | 3.06 | 18173 | 2448 | 2.60 | 168 | 0 | 1.62 |
| 20 h | 17750 | 3463 | 3.21 | 18013 | 3001 | 3.02 | 15765 | 2175 | 2.72 | 186 | 0 | 1.57 |
| 24 h | 19187 | 3711 | 3.10 | 18860 | 3048 | 2.99 | 16362 | 2362 | 2.66 | 483 | 33 | 1.63 |
| 36 h | | | | | | | | | | 961 | 80 | 1.82 |
| 48 h | | | | | | | | | | 1704 | 339 | 1.77 |

TABLE 11

Experimental results for lyoprotectants, at a 7:3 microcapsule to lyoprotectant solution ratio, and % of original bsh activity for *Lactobacillus reuteri* NCIMB 701359 at averaged values for 2 and 3 as well as 5 and 6 weeks.

| Lyoprotectant solutions shown to retain microcapsule morphology after lyophilization and rehydration | % of Original activity after lyophilization and storage at 4° C. | |
|---|---|---|
| | Weeks 2 and 3 | Weeks 5 and 6 |
| Free cells:(final concentration: 10% maltodextrin + 0.33% yeast extract) | | 100% (1, 2, 3 months at 4° C. and RT) |
| Microcapsules:1M Trehalose (7:3) (final conc. 0.3M) | 70.4% | 67.4% |
| Microcapsules:10% Maltodextrin (7:3) (final conc. 3%) | <25% | <25% |
| Microcapsules:1% Inulin (7:3) (final conc. 0.3%) | 83.1% | 85.3% |
| Microcapsules:10% Maltodextrin + 0.33% Yeast extract (7:3) (final conc. 3% + 0.1%) | 100% | 100% |
| Microcapsules:1M Trehalose + 0.33% Yeast extract (7:3) (final conc. 0.3M + 0.1%) | 69.2% | 65.2% |
| Microcapsules:1% Inulin + 0.33% Yeast extract (7:3) (final conc. 0.3% + 0.1%) | 75.2% | 80.5% |
| Microcapsules:10% Maltodextrin + 1% Casein hydrolysate (7:3) (final conc. 3% + 0.3%) | <25% | <25% |

TABLE 12

Experimental results for liquid storage conditions based on bsh activity (% original) at 4 days.

| Storage condition | % of original bsh activity after short term storage (4 days) at 4° C. |
|---|---|
| Microcapsules:Yogurt (3:97) | 87.1% (1 wks) |
| Microcapsules:Yogurt (3:97) | 54.6% (4 wks) |
| Microcapsules:Yogurt (3:97) | 53.5% (6 wks) |
| Microcapsules:Yogurt (1:1) | 96.0% |
| Microcapsules:5% Growth media (1:1) (final conc. 2.5%) | 92.6% |
| Microcapsules:10% Growth media (1:1) (final conc. 5%) | 92.4% |
| Microcapsules:20% Growth media (1:1) (final conc. 10%) | 88.2% |
| Microcapsules:100% Culture supernatant (1:1) (final conc. 50%) | 87.0% |
| Microcapsules:10% MRS (1:1) (final conc. 5%) | 81.5% |
| Microcapsules:1% Maltose (1:1) (final conc. 0.5%) | 22.0% |
| Microcapsules:1% Malt extract (1:1) (final conc. 0.5%) | <15% |
| Microcapsules:1% Inulin (1:1) (final conc. 0.5%) | <15% |
| Microcapsules:10% Sorbitol (1:1) (final conc. 5%) | <15% |
| Microcapsules:0.33% Yeast extract (1:1) (final conc. 0.165%) | <15% |
| Microcapsules:1% Inulin + 0.33% Yeast extract (1:1) (final conc. 0.5% + 0.165%) | <15% |
| Microcapsules:1M Fructose (1:1) (final conc. 0.5M) | <15% |
| Microcapsules:No liquid | <15% |
| Microcapsules:0.85% Saline (1:1) (final conc. 0.425%) | <15% |

TABLE 13

Experimental results for cryopreservative solution, when flash freezing and storing at −80° C., for *Lactobacillus reuteri* NCIMB 701359 microcapsules determined by microscopy for microcapsule morphology (% original quality) and HPLC for bsh activity (% original activity) data immediately after flash freezing in liquid nitrogen and after 3 weeks storage at −80° C.

| Cryopreservation Conditions | % of Original Quality Microcapsule Morphology | % of Original BSH activity Post-Flash freeze and thaw process | % of Original BSH activity Post-Flash freeze + storage (3 weeks) |
|---|---|---|---|
| Free cells:cells + 100% spent media (1:1) (final conc. 50%) | | 100% | |
| Microcapsules:1% maltodextrin + 0.23% yeast extract (1:1) (final conc. 0.5% + 0.115%) | | 77.8% | |
| Microcapsules:2% maltodextrin + 0.23% yeast extract (1:1) (final conc. 1% + 0.115%) | | 100% | |
| Microcapsules:10% maltodextrin + 0.33% yeast extract (1:1) (final conc. 5% + 0.165%) | | 100% | |
| Microcapsules:1% Inulin (1:1) (final conc. 0.5%) | 100% | 98.5% | 90.3% |
| Microcapsules:1M Trehalose (1:1) (final conc. 0.5M) | 98.3% | 100% | 88.3% |
| Microcapsules:1M Fructose (1:1) (final conc. 0.5M) | 98.2% | <50% | <50% |
| Microcapsules:1M Sucrose (1:1) (final conc. 0.5M) | 97.1% | 97.7% | 93.3% |
| Microcapsules:1M Lactose (1:1) (final conc. 0.5M) | 95.0% | 100% | 92.3% |
| Microcapsules:1M Maltose (1:1) (final conc. 0.5M) | 90.0% | 94.2% | 92.1% |
| Microcapsules:10% FOS (1:1) (final conc. 5%) | 70.0% | Not tested due to morphology | |
| Microcapsules:10% PEG8000 (1:1) (final conc. 5%) | 28.1% | Not tested due to morphology | |
| Microcapsules:10% Skim milk (1:1) (final conc. 5%) | 25.5% | Not tested due to morphology | |
| Microcapsules:10% Starch (1:1) (final conc. 5%) | 24.4% | Not tested due to morphology | |
| Microcapsules:0.85% Saline (1:1) (final conc. 0.425%) | 12.0% | Not tested due to morphology | |

TABLE 14

BSH activity, cell yield and stability of *L. reuteri* NCIMB 701359 grown in optimized media and harvested at different time points

| Harvest time (h) | BSH activity (U/mL culture/h) | BSH activity (U/g cell pellet/h) | Cell yield (g/mL) | Stability in final formulation |
|---|---|---|---|---|
| 0  | 0   | 0     | 0.000 | NA |
| 2  | 0   | 0     | 0.002 | NA |
| 4  | 0   | 0     | 0.005 | NA |
| 6  | 0   | 0     | 0.011 | NA |
| 8  | 153 | 10085 | 0.015 | Superior shelf life |
| 9  | 319 | 19071 | 0.017 | ↓ |
| 10 | 312 | 20559 | 0.015 | ↓ |
| 11 | 312 | 18746 | 0.017 | ↓ |
| 12 | 323 | 17364 | 0.019 | ↓ |
| 14 | 343 | 22644 | 0.015 | ↓ |
| 16 | 348 | 17618 | 0.020 | Inferior shelf life |

LIST OF REFERENCES

Angulo, P. "Nonalcoholic fatty liver disease." N. Engl. J. Med. 346, 1221 (2002).

Aso, Y. et al., "Preventive Effect of A *Lactobacillus*-Casei Preparation on the Recurrence of Superficial Bladder-Cancer in A Double-Blind Trial," European Urology 27(2), 104 (1995).

Chang, T. M. S. Semipermeable microcapsules. *Science* 146, 524-525 (1964).

Chang, T. M. & Prakash, S. Artificial cells for bioencapsulation of cells and genetically engineered *E. coli*. For cell therapy, gene therapy, and removal of urea and ammonia. *Methods Mol. Biol.* 63, 343-358 (1997).

Chang, T. M. & Prakash, S. Therapeutic uses of microencapsulated genetically engineered cells. *Mol. Med. Today* 4, 221-227 (1998).

Dobrogosz, W. J. "Enhancement of human health with *Lactobacillus reuteri*: A probiotic, immunobiotic and immunoprobiotic," *NUTRAfoods* 4, 15 (2005).

Ford, E. S. et al. Pevalence of metabolic syndrome among US adults: findings from the third National Health and Nutrition Examination Survey. JAMA 287(3):356 (2002).

Gaist, D. et al., "Lipid-lowering drugs and risk of myopathy: A population based follow-up study," 12(5), 565 (2001).

Gaist, D. et al., "Statins and risk of polyneuropathy—A case-control study," 58(9), 1333 (2002).

Goldenberg, I., M. Benderly, and U. Goldbourt, "Update on the use of fibrates: focus on bezafibrate," 4(1), 131 (2008).

Hallikainen, M. A. and M. I. J. Uusitupa, "Effects of 2 low-fat stanol ester-containing margarines on serum cholesterol concentrations as part of a low-fat diet in hypercholesterolemic subjects," 69(3), 403 (1999).

Huang, J. S. et al., "Efficacy of probiotic use in acute diarrhea in children: a meta-analysis," Dig. Dis. Sci. 47(11), 2625 (2002).

Jenkins, D. J. A. et al., "The effect on serum lipids and oxidized low-density lipoprotein of supplementing self-selected low-fat diets with soluble-fiber, soy, and vegetable protein foods," 49(1), 67 (2000).

Jones et al. "Method for Bile Acid Determination by High Performance Liquid Chromatography". J Med Sci 2003; 23(5):277-280.

Lodinova-Zadnikova, R. and U. Sonnenborn, "Effect of preventive administration of a nonpathogenic *Escherichia coli* strain on the colonization of the intestine with microbial pathogens in newborn infants," Biol. Neonate 71(4), 224 (1997).

Lopez-Garcia, E. "Consumption of Trans Fatty Acids Is Related to Plasma Biomarkers of Inflammation and Endothelial Dysfunction". The Journal of Nutrition 135 (3): 562 (2005).

McIntosh, G. H., P. J. Royle, and M. J. Playne, "A probiotic strain of *L. acidophilus* reduces DMH-induced large intestinal tumors in male Sprague-Dawley rats," Nutr. Cancer 35(2), 153 (1999).

Omar, M. A. and J. P. Wilson, "FDA adverse event reports on statin-associated rhabdomyolysis," 36(2), 288 (2002).

Ornish, D. et al., "Can Life-Style Changes Reverse Coronary Heart-Disease," 336(8708), 129 (1990).

Pedersen, T. R. et al., "Randomized Trial of Cholesterol-Lowering in 4444 Patients with Coronary-Heart-Disease—the Scandinavian Simvastatin Survival Study (4S)," 344(8934), 1383 (1994).

Pepys, M. B. et al., "Targeting C-reactive protein for the treatment of cardiovascular disease". Nature 440: 1217 (2006).

Prakash, S. and Jones M. L. Engineering Artificial Cells for Therapy. 7-22-2002. Sarawak, Malaysia, 2nd World Engineering Congress. Ref Type: Conference Proceeding Prakash, S. and Urbanska A. M. (2007). Fermented milk product and uses thereof. WO 2007/140613.

Probstfield, J. L. and B. M. Rifkind, "The Lipid Research Clinics Coronary Primary Prevention Trial: design, results, and implications," 40 Suppl 1, S69-S75 (1991).

Rayes, N. et al., "Early enteral supply of *lactobacillus* and fiber versus selective bowel decontamination: a controlled trial in liver transplant recipients," Transplantation 74(1), 123 (2002).

Scalia. "Simultaneous determination of free and conjugated bile acids in human gastric juice by HPLC". J of Chrom, 431 (1988) 259-269.

Sgro, C. and A. Escousse, "Side-Effects of Hypolipidemic Drugs," 46(5), 351 (1991).

Staffa, J. A., J. Chang, and L. Green, "Cerivastatin and reports of fatal rhabdomyolysis," 346(7), 539 (2002).

Szajewska, H. et al., "Efficacy of *Lactobacillus* GG in prevention of nosocomial diarrhea in infants," J. Pediatr. 138(3), 361 (2001).

Tabas, K. J. Williams, and J. Boren, "Subendothelial lipoprotein retention as the initiating process in atherosclerosis—Update and therapeutic implications," 116 (16), 1832 (2007).

Tall, A. R. "An overview of reverse cholesterol transport," 19 Suppl A, A31-A35 (1998).

"Third Report of the National Cholesterol Education Program (NCEP) Expert Panel on Detection, Evaluation, and Treatment of High Blood Cholesterol in Adults (Adult Treatment Panel III) final report," 106(25), 3143 (2002).

Tobias, P. S., L. K. Curtiss, "Toll-like receptors in atherosclerosis," Biochem Soc Trans. 35(6) 1453 (2007).

Uludag, H., De Vos, P., & Tresco, P. A. Technology of mammalian cell encapsulation. *Adv. Drug Deliv. Rev.* 42, 29-64 (2000).

Urbanska A. M., Bhathena J., Martoni C., Prakash S. "Estimation of the Potential Antitumor Activity of Microencapsulated *Lactobacillus acidophilus* Yogurt Formulation in the Attenuation of Tumorigenesis in Apc(Min/+) Mice". *Dig. Dis. Sci.* (2009) 54:264-273.

The invention claimed is:

1. A bile salt hydrolase (BSH) active bacteria, comprising a first BSH activity that results from growth in an optimized plurality of growth medium components, wherein said first BSH activity is between 6.1 and 113.6 fold higher than a second BSH activity that results from the growth of said BSH active bacteria in de Man, Rogosa, Sharpe (MRS) medium.

2. The BSH active bacteria of claim 1, wherein said first BSH activity is between 8.9 and 113.6 fold higher than said second BSH activity.

3. The BSH active bacteria of claim 2, wherein said first BSH activity is between 39.7 and 113.6 fold higher than said second BSH activity.

4. The highly BSH active bacteria of claim 3, wherein said first BSH activity is between 84.8 and 113.6 fold higher than said second BSH activity.

5. An oral composition, comprising the BSH active bacteria of claim 2; wherein said first BSH activity degrades >2253 μmol glycodeoxycholic acid (GDCA)/gram wet bacterial pellet/hr when measured over 30 minutes, wherein said high BSH activity is stable so that at least about 69.2% of said BSH activity is retained when said highly BSH active bacteria are stored for a time period of at least 3 weeks.

6. The oral composition of claim 5, wherein said first BSH activity degrades >15000 μmol GDCA/g/hr when measured over 30 minutes.

7. The BSH active bacteria of claim 1, wherein the BSH active bacteria is *Lactobacillus, Bifidobacteria, Pediococcus, Streptococcus, Enterococcus,* or *Leuconostoc.*

8. The BSH active bacteria of claim 7, wherein the bacteria is *Lactobacillus.*

9. The BSH active bacteria of claim 8, wherein the *Lactobacillus* is *Lactobacillus reuteri.*

10. The BSH active bacteria of claim 9, wherein the *Lactobacillus reuteri* is *Lactobacillus reuteri* (NCIMB 701359), *Lactobacillus reuteri* (NCIMB 701089), *Lactobacillus reuteri* (ATCC 55148), *Lactobacillus reuteri* (ATCC 23272), *Lactobacillus reuteri* (NCIMB 702655), *Lactobacillus reuteri* (LMG 18238), *Lactobacillus reuteri* (CCUG 32271), *Lactobacillus reuteri* (CCUG 32305), *Lactobacillus reuteri* (CCUG 37470), *Lactobacillus reuteri* (CCUG 44001) or *Lactobacillus reuteri* (CCUG 44144).

11. The BSH active bacteria of claim 10, wherein the *Lactobacillus reuteri* is *Lactobacillus reuteri* (NCIMB 701359).

12. The oral composition of claim 6, wherein the bacteria is *Lactobacillus.*

13. The oral composition of claim 12, wherein the *Lactobacillus* is *Lactobacillus reuteri.*

14. The oral composition of claim 13, wherein the *Lactobacillus reuteri* is *Lactobacillus reuteri* (NCIMB 701359).

15. The BSH active bacteria of claim 1, wherein said optimized plurality of growth medium components comprises:
   a. a carbon source comprising maltose or a combination of inulin and glucose; and
   b. a nitrogen source comprising yeast extract, malt extract, and peptone No. 3;
wherein said growth medium components are in a growth medium having a pH of 5-7.

16. The BSH active bacteria of claim 15, wherein the optimized plurality of growth medium components further comprises a reducing agent.

17. The oral composition of claim 16, wherein the reducing agent is cysteine.

18. The BSH active bacteria of claim 1, wherein the bacteria are immobilized in a polymer or are encapsulated in polymeric semi permeable microcapsules or nanocapsules.

19. The oral composition of claim 3, wherein said first BSH activity has been stabilized by lyophilizing, heat drying, spray drying, or flash freezing said BSH active bacteria following said growth in said plurality of growth medium components.

20. The oral composition of claim 19, wherein said BSH active bacteria are lyophilized with lyoprotectants comprising (a) 0.2 to 10% maltodextrin and 0.05 to 0.33% yeast extract, (b) 0.05 to 10% inulin and 0.05 to 0.33% yeast extract, (c) 0.05 to 10% inulin, (d) 1M Trehalose, or (e) 1M trehalose and 0.33% yeast extract.

21. The oral composition of claim 3, wherein said first BSH activity has been stabilized by flash freezing said BSH active bacteria in a cryoprotectant solution comprising a final concentration of (a) 0.2 to 10% maltodextrin and 0.05 to 0.33% yeast extract, (b) 0.05 to 10% inulin, (c) 0.5M Trehalose, (d) 0.5M sucrose, (e) 0.5M lactose, (f) 0.5M maltose, or (g) 50-99.99% spent media.

22. The oral composition of claim 5, wherein the oral composition further comprises a triglyceride lowering agent, an agent for increasing HDL or limiting HDL decrease, a cholesterol lowering agent, an agent for preserving BSH activity, an agent for modulating adipokines or hormones of obesity, a hypoglycemic agent, a therapeutic for reducing the pro-inflammatory cytokines IL-la/B, IL-2, IL-15, IL-3, IL-6, IL-8, IL-12, IL-17, IFN-gamma, TNF-alpha, or for increasing the level of the anti-inflammatory cytokines IL-1ra, IL-9, IL-10, IL-11, vitamin B12, conjugated linoleic acid (CLA), reuterin, or reutericyclin.

\* \* \* \* \*